US012214085B2

(12) United States Patent
MohanKumar et al.

(10) Patent No.: US 12,214,085 B2
(45) Date of Patent: *Feb. 4, 2025

(54) NANOPARTICLES FOR PREVENTING PERI/POST-MENOPAUSAL BONE LOSS AND/OR OBESITY

(71) Applicant: University of Georgia Research Foundation, Inc., Athens, GA (US)

(72) Inventors: Sheba M. J. MohanKumar, Athens, GA (US); Puliyur S. MohanKumar, Athens, GA (US); Yen-Jun Chuang, Athens, GA (US)

(73) Assignee: UNIVERSITY OF GEORGIA RESEARCH FOUNDATION, INC., Athens, GA (US)

( * ) Notice: Subject to any disclaimer, the term of this patent is extended or adjusted under 35 U.S.C. 154(b) by 103 days.

This patent is subject to a terminal disclaimer.

(21) Appl. No.: 17/835,684

(22) Filed: Jun. 8, 2022

(65) Prior Publication Data

US 2022/0387334 A1 Dec. 8, 2022

Related U.S. Application Data

(60) Provisional application No. 63/208,390, filed on Jun. 8, 2021.

(51) Int. Cl.
*A61K 9/51* (2006.01)
*A61K 38/47* (2006.01)
(52) U.S. Cl.
CPC ............ *A61K 9/5123* (2013.01); *A61K 38/47* (2013.01)
(58) Field of Classification Search
CPC ............................. A61K 9/5123; A61K 38/47
See application file for complete search history.

(56) References Cited

U.S. PATENT DOCUMENTS

| | | | | |
|---|---|---|---|---|
| 5,378,688 | A | 1/1995 | Nett et al. | |
| 2009/0239795 | A1* | 9/2009 | Ballance .................. | A61P 3/10 435/254.2 |

(Continued)

FOREIGN PATENT DOCUMENTS

| | | | |
|---|---|---|---|
| CN | 107998404 | A | 5/2018 |
| CN | 108524935 | A | 9/2018 |

(Continued)

OTHER PUBLICATIONS

International Search Report received for PCT Patent Application No. PCT/US2022/032645, mailed on Dec. 2, 2022, 5 pages.

(Continued)

*Primary Examiner* — Jianfeng Song
(74) *Attorney, Agent, or Firm* — PABST PATENT GROUP LLP

(57) ABSTRACT

Nanoparticles and formulations for preventing or reducing peri-/post-menopausal bone loss and/or obesity in a subject are disclosed. The nanoparticles contain a cage, such as a zeolitic imidazolate framework ("ZIF"), a surface modifying agent, a targeting ligand, and an active agent. The surface modifying agent is attached to the outer surface of the cage and the targeting ligand is exposed to the surrounding environment. The active agent is encapsulated in the cage. The targeting ligand binds to a reproductive hormone or a receptor of a reproductive hormone. The active agent can be a ribosome inactivating protein, an apoptosis inducer, a hormone, a receptor ligand, or a nucleic acid, or a combination thereof, that inactivate ribosomes of gonadotroph cells and/or prevent or reduce secretion of follicle-stimulating hormones in the subject. Uses for formulations incorporating the nanoparticles for preventing or reducing peri-/post-menopausal bone loss and/or obesity in a subject are also disclosed.

19 Claims, 3 Drawing Sheets

(56) References Cited

U.S. PATENT DOCUMENTS

| | | |
|---|---|---|
| 2015/0359900 A1 | 12/2015 | Wang et al. |
| 2019/0270822 A1 | 9/2019 | Ayres et al. |
| 2022/0177494 A1* | 6/2022 | Gong .................. A61K 9/0019 |
| 2022/0387335 A1 | 12/2022 | Mohankumar et al. |
| 2022/0387336 A1 | 12/2022 | Mohankumar et al. |

FOREIGN PATENT DOCUMENTS

| | | |
|---|---|---|
| WO | 2018187478 A1 | 10/2018 |
| WO | 2021097194 A1 | 5/2021 |
| WO | 2021103232 A1 | 6/2021 |

OTHER PUBLICATIONS

International Search Report received for PCT Patent Application No. PCT/US2022/032652, mailed on Sep. 19, 2022, 5 pages.

International Search Report received for PCT Patent Application No. PCT/US2022/032683, mailed on Sep. 23, 2022, 5 pages.

Bellina, et al., "Regioselective Functionalization of the Imidazole Ring via Transition Metal-Catalyzed C—N and C—C Bond Forming Reactions", Advanced Synthesis & Catalysis, vol. 352, No. 8, Sep. 2010, pp. 1223-1276.

Chen, et al., "Derivative of Epigallocatechin-3-gallatea Encapsulated in ZIF-8 with Polyethylene Glycol-Folic Acid Modification for Target and pH-Responsive Drug Release in Anticancer Research", ACS Biomater. Sci. Eng, vol. 4, No. 12, Dec. 10, 2018, pp. 4183-4192.

Jian, et al., "Water-based synthesis of zeolitic imidazolate framework-8 with high morphology level at room temperature", RSC Advances. Vol. 5, No. 60, 2015, pp. 48433-48441.

Kawai, et al., "Serum follicle-stimulating hormone level is a predictor of bone mineral density in patients with hormone replacement therapy", Arch Gynecol Obstet, vol. 269, No. 3, Mar. 2004, pp. 192-195.

Kuroda, et al., "Saporin toxin-conjugated monoclonal antibody targeting prostate-specific membrane antigen has potent anticancer activity", Prostate, vol. 70, No. 12, Jul. 8, 2010, pp. 1286-1294.

Labrie, et al., "Gonadotropin-releasing hormone agonists in the treatment of prostate cancer", Endocr Rev, vol. 26 No. 3, May 2, 2005., pp. 361-379.

Liu, et al., "Blocking FSH Induces Thermogenic Adipose Tissue and Reduces Body Fat", Nature, vol. 546, No. 7656, Jun. 1, 2017, pp. 107-112.

Lu, et al., "A Review on Polymer and Lipid-Based Nanocarriers and Its Application to Nano-Pharmaceutical and Food-Based Systems", Front Nutr., vol. 8, No. 783831, Dec. 1, 2021, 13 pages.

Mitchell, et al., "Engineering precision nanoparticles for drug delivery", Nat Rev Drug Discov., vol. 20, No. 2, Feb. 2021, pp. 101-124.

Qin, et al., "pH-Responsive Polymer-Stabilized ZIF-8 Nanocomposites for Fluorescence and Magnetic Resonance Dual-Modal Imaging-Guided Chemo-/Photodynamic Combinational Cancer Therapy", ACS Appl Mater Interfaces., vol. 11, No. 37, Sep. 18, 2019, pp. 34268-34281.

Randolph, et al., "The value of follicle-stimulating hormone concentration and clinical findings as markers of the late menopausal transition", J Clin Endocrinol Metab., vol. 91, No. 8, Aug. 2006, pp. 3034-3040.

Shieh, et al., "Water-Based Synthesis of Zeolitic Imidazolate Framework-90 (ZIF-90) with a Controllable Particle Size", Chemistry, vol. 19, No. 34, Aug. 19, 2013, pp. 11139-11142.

Sowers, et al., "Endogenous hormones and bone turnover markers in pre- and perimenopausal women: SWAN", Osteoporos Int., vol. 14, No. 3, May 2003, pp. 191-197.

Vallet-Regí, et al., "Mesoporous Silica Nanoparticles for Drug Delivery: Current Insights", Molecules, vol. 23, No. 47, Jan. 2018, 19 pages.

Wang, et al., "State of the Art and Prospects in Metal-Organic Framework (MOF)-Based and MOF-Derived Nanocatalysis", Chem Rev., vol. 120, No. 2, Jan. 22, 2020, pp. 1438-1511.

Kalyanaraman, et al., "Doxorubicin-induced apoptosis: implications in cardiotoxicity", Molecular and Cellular Biochemistry, vol. 234-235, No. 1-2, 2002, pp. 119-124.

* cited by examiner

NANOPARTICLES FOR PREVENTING PERI/POST-MENOPAUSAL BONE LOSS AND/OR OBESITY

CROSS-REFERENCE TO RELATED APPLICATION

This application claims benefit of and priority to U.S. Provisional Application No. 63/208,390 filed Jun. 8, 2021, which is incorporated herein by reference in its entirety.

FIELD OF THE INVENTION

This invention is generally in the field of compositions for treating peri-/post-menopausal bone loss and/or obesity.

BACKGROUND OF THE INVENTION

Significant bone loss starts to occur in women approximately 2-3 years before entering menopause. During this time, follicle-stimulating hormone (FSH) levels are high and estrogen levels are low (Randolph, et al., *J Clin Endocrinol Metab*, 2006, 91(8):3034-40; Sowers, et al., *Osteoporos Int*, 2003, 14(3):191-7). Estrogen replacement therapy after menopause does not bring back FSH levels to the premenopausal levels (Kawai, et al., Arch Gynecol Obstet, 2004, 269(3):192-5). Further, women continue to lose bone and gain weight (Liu, et al., Nature, 2017, 546(7656):107-112) when undergoing estrogen replacement therapy.

Currently available anti-obesity agents, which are known to reduce appetite or interfere with nutrient absorption, have not been successful in helping women during perimenopause or post-menopause due to the complications related to poor efficacy and side effects.

There remains a need for improved compositions and methods for preventing or reducing peri-/post-menopausal bone loss and/or obesity.

Therefore, it is the object of the present invention to provide compositions for preventing or reducing peri-/post-menopausal bone loss and/or obesity in subject in need thereof.

It is a further object of the present invention to provide pharmaceutical formulations for preventing or reducing peri-/post-menopausal bone loss and/or obesity in a subject in need thereof.

It is a further object of the present invention to provide methods for preventing or reducing peri-/post-menopausal bone loss and/or obesity in a subject in need thereof.

SUMMARY OF THE INVENTION

Nanoparticles and formulations for preventing or reducing peri-/post-menopausal bone loss and/or obesity are disclosed herein. Also disclosed are uses for the nanoparticles and formulations incorporating the nanoparticles.

The nanoparticles for preventing or reducing peri-/post-menopausal bone loss and/or obesity contains cage, such as a zeolitic imidazolate framework ("ZIF"), a surface modifying agent, a targeting ligand, and an active agent. The cage is a 3-dimensional structure that contains an opening for encapsulating a substance therein. Suitable materials for forming the cage of the nanoparticles include ZIFs and other metal-organic frameworks, such as organic-inorganic hybrid crystalline porous materials and those described in Wang, et al., Chem. Rev. 120(2):1438-1511 (2020); lipids, such as phospholipids, sterols, sphingolipids, PEGylated lipids, glycerolipids, anionic lipids, and cationic lipids, e.g. those described in Lu, et al., Frontiers in Nutrition, 8:783831 (2021) and Mitchell, et al., Nature Reviews, 20:101 (2021); polymers, such as polymersomes, dendrimers, polymeric micelles, and nanospheres, e.g. those described in Lu, et al., Frontiers in Nutrition, 8:783831 (2021) and Mitchell, et al., Nature Reviews, 20:101 (2021); and inorganic materials, such as silica, e.g. mesoporous silica and those described in Vallet-Regi, et al., Molecules, 23(47):23010047 (2018). Typically, the surface modifying agent is attached to the outer surface of the cage and the targeting ligand is exposed to the surrounding environment. The active agent is encapsulated in the cage. For example, the surface modifying ligand is attached to the outer surface of the ZIF and the targeting ligand is exposed to the surrounding environment. The active agent is encapsulated in the ZIF.

When the cage of the nanoparticles is a ZIF, the ZIF contains a metal ion and an imidazolate linker. The imidazolate linker may be un-modified or functionalized with amine, hydroxyl, thiol, aldehyde, or carboxyl, or a combination thereof.

Optionally, the targeting ligand is conjugated to the surface modifying agent. At least 20 wt % (weight of the surface modifying agent conjugated to the targeting ligand/total weight of the surface modifying agent attached to the cage) of the surface modifying agent is conjugated to the targeting ligand. For example, at least 20 wt % (weight of the surface modifying agent conjugated to the targeting ligand/total weight of the surface modifying agent attached to the ZIF) of the surface modifying agent is conjugated to the targeting ligand.

The surface modifying agent contains a polymer backbone, such as a polyalkylene glycol backbone (e.g. polyethylene glycol backbone) or a poly(lactic-co-glycolic acid) backbone. The surface modifying agent can ionically bind to the outer surface of the cage through a charged chemical moiety that is conjugated to one end of the surface modifying agent, such as folate, L-methylfolate, or glutamate, or a combination thereof. For example, the surface modifying agent is ionically bound to the outer surface of the ZIF through a charged chemical moiety that is conjugated to one end of the surface modifying agent, such as folate, L-methylfolate, or glutamate, or a combination thereof.

The nanoparticles generally have an average diameter (including the surface modifying agent) of less than 100 nm and at least 10 nm, and a surface density of the surface modifying agent ("SMA") of at least 1 $SMA/nm^2$.

Typically, the targeting ligand binds to a receptor of a reproductive hormone, such as a receptor of a gonadotropin-releasing hormone ("GnRH") or a follicle stimulating hormone ("FSH").

The description below describes nanoparticles that contain a ZIF cage. However, these descriptions apply to other suitable materials for forming the cage, as well, such as those described above. Thus references to a "ZIF" or "ZIF cage" herein also generally apply to other suitable materials for forming a cage of the nanoparticles.

The active agent encapsulated in the ZIF is provided in an effective amount to reduce or prevent bone loss and/or obesity in the subject. The active agent encapsulated in the ZIF can be a substance that inactivates ribosomes of gonadotroph cells induces apoptosis of gonadotroph cells, reduces or prevent secretion of FSH, and/or reduces the FSH level in a subject. Examples of active agents suitable for encapsulation in the ZIF are ribosome inactivating proteins, apoptosis inducer, hormones, receptor ligands, or nucleic acids, or a combination thereof. Optionally, the nanoparticles further include a diagnostic agent encapsulated in the ZIF, such as a fluorescent molecule.

Pharmaceutical formulations containing a plurality of the nanoparticles described herein and a pharmaceutically acceptable carrier and/or excipient are disclosed. The pharmaceutical formulations can be in a suitable form for intramuscular administration, intravenous administration, intraperitoneal administration, or subcutaneous administration, or a combination thereof. Typically, the active agent is included in the pharmaceutical formulation in an effective amount to reduce or prevent bone loss, reduce body weight, reduce percentage of fat, and/or reduce body mass index (BMI) of a subject.

For example, the amount of the active agent in the pharmaceutical formulation is effective to reduce the body weight, reduce the percentage of fat, and/or reduce the body mass index ("BMI") of the subject by at least 5%, at least 10%, at least 15%, at least 20%, at least 25%, or at least 30% compared to the body weight, the percentage of fat, and/or the BMI of the subject before treatment. For example, the amount of the active agent in the pharmaceutical formulation is effective to reduce bone loss in the subject as shown by an increase or decrease of an osteoporosis biomarker level in the blood of the subject by at least 5%, at least 10%, at least 15%, at least 20%, at least 25%, or at least 30% compared to the osteoporosis biomarker level in the blood of the subject before treatment. Examples of osteoporosis biomarkers suitable for showing the reduction of bone loss in a subject include, but are not limited to, osteocalcin, bone specific alkaline phosphatase, PINP, PICP, NTX-1, TRAP5B, osteopontin, and bone sialoprotein, and a combination thereof. For example, the amount of the active agent in the pharmaceutical formulation is effective to reduce bone loss in the subject as shown by an increase of the osteocalcin, bone specific alkaline phosphatase, PINP, and/or PICP level in the blood of the subject by at least 5%, at least 10%, at least 15%, at least 20%, at least 25%, or at least 30% compared to the osteocalcin, bone specific alkaline phosphatase, PINP, and/or PICP level in the blood of the subject before treatment. For example, the amount of the active agent in the pharmaceutical formulation is effective to reduce bone loss in the subject as shown by a decrease of the NTX-1, TRAP5B, osteopontin, and/or bone sialoprotein level in the blood of the subject by at least 5%, at least 10%, at least 15%, at least 20%, at least 25%, or at least 30% compared to the NTX-1, TRAP5B, osteopontin, and/or bone sialoprotein level in the blood of the subject before treatment.

Methods for preventing or reducing peri-/post-menopausal bone loss and/or obesity in a subject in need thereof using the pharmaceutical formulations described herein are also disclosed. The method includes administering to the subject the pharmaceutical formulation, where the administration step occurs one or more times. Following a single administration or more than one administration of the pharmaceutical formulation, an effective amount of the nanoparticles to reduce or prevent bone loss, reduce body weight, reduce percentage of fat, and/or reduce body mass index (BMI) of the subject is administered to the subject. The subject can be a peri/post-menopausal mammal.

BRIEF DESCRIPTION OF THE DRAWINGS

FIG. 3A shows the fluorescent emission of the nanoparticles excited at 600 nm. FIG. 3B shows the fluorescent emission of the nanoparticles excited at 645 nm.

DETAILED DESCRIPTION OF THE INVENTION

I. Nanoparticles

Figure 1A:
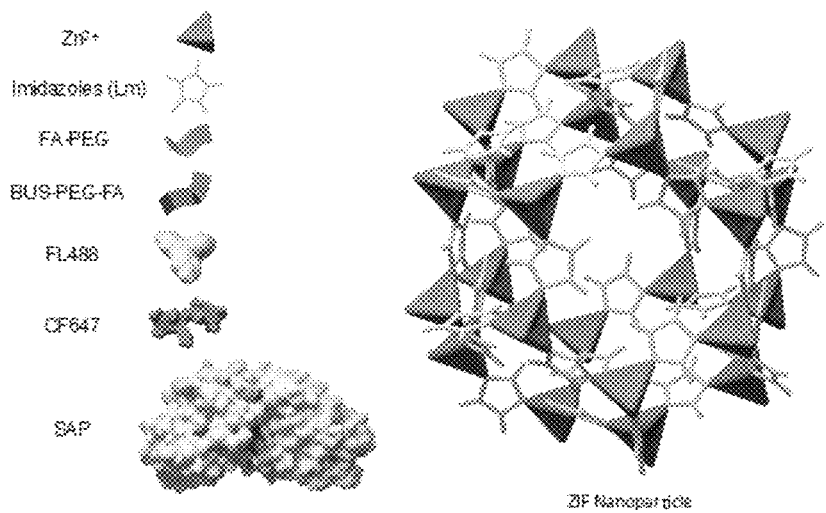
FIG. 1A is a schematic showing the components forming an exemplary nanoparticle.

Nanoparticles for preventing or reducing peri-/post-menopausal bone loss and/or obesity are described herein. Generally, the nanoparticles contain a cage, a surface modifying agent, a targeting ligand, and an active agent. For example, the cage forming the nanoparticles is a zeolitic imidazolate framework (also referred herein as "ZIF"). The cage is a 3-dimensional structure that contains an opening for encapsulating a substance therein. Suitable materials for forming the cage of the nanoparticles include ZIF and other metal-organic frameworks, such as organic-inorganic hybrid crystalline porous materials and those described in Wang, et al., Chem. Rev. 120(2):1438-1511 (2020); lipids, such as phospholipids, sterols, sphingolipids, PEGylated lipids, glycerolipids, anionic lipids, and cationic lipids, e.g. those described in Lu, et al., Frontiers in Nutrition, 8:783831 (2021) and Mitchell, et al., Nature Reviews, 20:101 (2021); polymers, such as polymersome, dendrimers, polymeric micelles, and nanospheres, e.g. those described in Lu, et al., Frontiers in Nutrition, 8:783831 (2021) and Mitchell, et al., Nature Reviews, 20:101 (2021); and inorganic materials, such as silica, e.g. mesoporous silica and those described in Vallet-Regi, et al., Molecules, 23(47):23010047 (2018).

The surface modifying ligand can be attached to the outer surface of the cage. Typically, the targeting ligand is arranged on the outer surface of the cage such that it is exposed to the surrounding environment. Optionally, the targeting ligand is conjugated to the surface modifying ligand and is exposed to the surrounding environment. The active agent can be encapsulated in the cage.

For example, the surface modifying agent is attached to the outer surface of the ZIF. The targeting ligand is arranged on the outer surface of the ZIF such that it is exposed to the surrounding environment. Optionally, the targeting ligand is conjugated to the surface modifying agent and is exposed to the surrounding environment. The active agent can be encapsulated in the ZIF.

The nanoparticles can degrade in an acidic environment (i.e. pH<6.5, such as in a range from 4.5 to about 5.0) and thereby release the active agent. For example, following intravenous administration of the nanoparticles in a subject, such as a mammal, the nanoparticles remain intact in an environment having physiological pH (i.e. pH>6.5, such as in a range from about 6.5 to about 8.0). After the nanoparticles are engulfed by the cell membrane and enter the cell, they are delivered to the lysosomes which generally maintain an acidic pH, such as from about 4.5 to about 5.0, in which the nanoparticles degrade.

The overall charge of the nanoparticles is generally neutral or near neutral.

A. Components

1. ZIF

The cage of the nanoparticles may be a ZIF. ZIFs are metal-organic frameworks formed by metal ions and imidazolate linkers. Any suitable ZIF may be used in the nanoparticles. Preferably, the ZIFs suitable for use in the nanoparticles are synthesized using water-based preparation conditions to maintain the biological activities of the targeting ligands and the active agents of the nanoparticles. For example, suitable ZIFs and water-based synthesis methods for making ZIFs are described in Jian, et al., *RSC Adv.*, 5:48433 (2015) and Shieh, et al., *Chem. Eur. J.*, 19:11139 (2013).

For example, a ZIF can be formed through three-dimensional assembly of tetrahedrally-coordinated metal-imidazolate building units corresponding to a general Formula (I) below:

Formula (I)

in which:

M represents a metal ion;

Each of $L_1$, $L_2$, $L_3$, and $L_4$ represents an imidazolate linker; they may be the same or different;

The metal ion binds to each of the imidazolate linkers $L_1$, $L_2$, $L_3$, and $L_4$ via a nitrogen atom of the imidazolate linker.

Each solid line in Formula (I) indicates a coordinate covalent bond.

The ZIF can have any suitable crystal structure, such as ZIF-2, ZIF-3, ZIF-4, ZIF-8, ZIF-10, ZIF-11, ZIF-12, ZIF-14, ZIF-20, ZIF-21, ZIF-60, ZIF-61, ZIF-62, ZIF-64, ZIF-65, ZIF-66, ZIF-67, ZIF-68, ZIF-69, ZIF-70, ZIF-71, ZIF-72, ZIF-73, ZIF-74, ZIF-75, ZIF-76, ZIF-77, ZIF-78, ZIF-81, ZIF-82, ZIF-90, ZIF-91, ZIF-92, ZIF-95, or ZIF-100. For example, the ZIF has a crystal structure of ZIF-90.

a. Metal Ions

The ZIF can include building units as shown in Formula (I), containing a metal ion.

Examples of metal ions contained in a building unit of ZIF include, but are not limited to, $Li^+$, $Na^+$, $K^+$, $Rb^+$, $Cs^+$, $Be^{2+}$, $Mg^{2+}$, $Ca^{2+}$, $Sr^{2+}$, $Ba^{2+}$, $Sc^{3+}$, $Sc^{2+}$, $Sc^+$, $Y^{3+}$, $Y^{2+}$, $Y^+$, $Ti^{4+}$, $Ti^{3+}$, $Ti^{2+}$, $Zr^{4+}$, $Zr^{3+}$, $Zr^{2+}$, $Hf^{4+}$, $Hf^{3+}$, $V^{5+}$, $V^{4+}$, $V^{3+}$, $V^{2+}$, $Nb^{5+}$, $Nb^{4+}$, $Nb^{3+}$, $Nb^{2+}$, $Ta^{5+}$, $Ta^{4+}$, $Ta^{3+}$, $Ta^{2+}$, $Cr^{6+}$, $Cr^{5+}$, $Cr^{4+}$, $Cr^{3+}$, $Cr^{2+}$, $Mo^{6+}$, $Mo^{5+}$, $Mo^{4+}$, $Mo^+$, $Mo^{2+}$, $Mo^+$, $W^{6+}$, $W^{5+}$, $W^{4+}$, $W^{3+}$, $W^{2+}$, $W^+$, $Mn^{7+}$, $Mn^{6+}$, $Mn^{5+}$, $Mn^{4+}$, $Mn^{3+}$, $Mn^{2+}$, $Mn^+$, $Re^{7+}$, $Re^{6+}$, $Re^{5+}$, $Re^{4+}$, $Re^{3+}$, $Re^{2+}$, $Re^+$, $Fe^{6+}$, $Fe^{4+}$, $Fe^{3+}$, $Fe^{2+}$, $Fe^+$, $Ru^{8+}$, $Ru^{7+}$, $Ru^{6+}$, $Ru^{4+}$, $Ru^{3+}$, $Ru^{2+}$, $Os^{8+}$, $Os^{7+}$, $Os^{6+}$, $Os^{5+}$, $Os^{4+}$, $Os^{3+}$, $Os^{2+}$, $Os^+$, $Co^{5+}$, $Co^{4+}$, $Co^{3+}$, $Co^{2+}$, $Co^+$, $Rh^{6+}$, $Rh^{5+}$, $Rh^{4+}$, $Rh^{3+}$, $Rh^{2+}$, $Rh^+$, $Ir^{6+}$, $Ir^{5+}$, $Ir^{4+}$, $Ir^{3+}$, $Ir^{2+}$, $Ir^+$, $Ni^{3+}$, $Ni^{2+}$, $Ni^+$, $Pd^{6+}$, $P^{d4+}$, $P^{d2+}$, $Pd^+$, $Pt^{6+}$, $Pt^{5+}$, $Pt^{4+}$, $Pt^{3+}$, $Pt^{2+}$, $Pt^+$, $Cu^{4+}$, $Cu^{3+}$, $Cu^{2+}$, $Cu^+$, $Ag^{3+}$, $Ag^{2+}$, $Ag^+$, $Au^{5+}$, $Au^{4+}$, $Au^{3+}$, $Au^{2+}$, $Au^+$, $Zn^{2+}$, $Zn^+$, $Cd^{2+}$, $Cd^+$, $Hg^{4+}$, $Hg^{2+}$, $Hg^+$, $B^{3+}$, $B^{2+}$, $B^+$, $Al^{3+}$, $Al^{2+}$, $Al^+$, $Ga^{3+}$, $Ga^{2+}$, $Ga^+$, $In^{3+}$, $In^{2+}$, $In^+$, $Tl^{3+}$, $Tl^+$, $Si^{4+}$, $Si^{3+}$, $Si^{2+}$, $Si^+$, $Ge^{4+}$, $Ge^{3+}$, $Ge^{2+}$, $Ge^+$, $Sn^{4+}$, $Sn^{2+}$, $Pb^{4+}$, $Pb^{2+}$, $As^{5+}$, $As^{3+}$, $As^{2+}$, $As^+$, $Sb^{5+}$, $Sb^{3+}$, $Bi^{5+}$, $Bi^{3+}$, $Te^{6+}$, $Te^{5+}$, $Te^{4+}$, $Te^{2+}$, $La^{3+}$, $La^{2+}$, $Ce^{4+}$, $Ce^{3+}$, $Ce^{2+}$, $Pr^{4+}$, $Pr^{3+}$, $Pr^{2+}$, $Nd^{3+}$, $Nd^{2+}$, $Sm^{3+}$, $Sm^{2+}$, $Eu^{3+}$, $Eu^{2+}$, $Gd^{3+}$, $Gd^{2+}$, $Gd^+$, $Tb^{4+}$, $Tb^{3+}$, $Tb^{2+}$, $Tb^+$, $db^{3+}$, $db^{2+}$, $Ho^{3+}$, $Er^{3+}$, $Tm^{4+}$, $Tm^{3+}$, $Tm^{2+}$, $Yb^{3+}$, $Yb^{2+}$, $Lu^{3+}$, $La^{3+}$, $La^{2+}$, $La+$.

Optionally, the metal ion contained in a building unit of ZIF is $Be^{2+}$, $Mg^{2+}$, $Ca^{2+}$, $Sr^{2+}$, $Ba^{2+}$, $Sc^{2+}$, $Y^{3+}$, $Ti^{2+}$, $Zr^{2+}$, $V^{2+}$, $Nb^{2+}$, $Ta^{2+}$, $Cr^{2+}$, $Mo^{2+}$, $W^{2+}$, $Mn^{2+}$, $Re^{2+}$, $Fe^{2+}$, $Ru^{2+}$, $Os^{2+}$, $Co^{2+}$, $Rh^{2+}$, $Ir^{2+}$, $Ni^{2+}$, $Pd^{2+}$, $Pt^{2+}$, $Cu^{2+}$, $Ag^{2+}$, $Au^{2+}$, $Zn^{2+}$, $Cd^{2+}$, $Hg^{2+}$, $B^{2+}$, $Al^{2+}$, $Ga^{2+}$, $In^{2+}$, $Si^{2+}$, $Ge^{2+}$, $Sn^{2+}$, $Pb^{2+}$, $As^{2+}$, $Te^{2+}$, $La^{2+}$, $Ce^{2+}$, $Pr^{2+}$, $Nd^{2+}$, $Sm^{2+}$, $Eu^{2+}$, $Gd^{2+}$, $Tb^{2+}$, $db^{2+}$, $Tm^{2+}$, or $Yb^{2+}$.

Optionally, the metal ion contained in a building unit of ZIF is $Zn^+$, $Zn^{2+}$, $Pd^{2+}$, $Pd^{4+}$, $Pt^{2+}$, $Pt^{4+}$, $Ni^+$, $Ni^{2+}$, $Ni^{3+}$, $Mn^{2+}$, $Mn^{3+}$, $Mn^{4+}$, $Mn^{6+}$, $Mn^{7+}$, $Co^{2+}$, $Co^{3+}$, $Cu^{2+}$, $Cd^{2+}$, $Fe^{2+}$, $Fe^{3+}$, and $Ti^{4+}$.

The ZIF structure can include building units containing a single type of metal ion as described above, such as $Zn^+$, $Zn^{2+}$, $Pd^{2+}$, $Pd^{4+}$, $Pt^{2+}$, $Pt^{4+}$, $Ni^+$, $Ni^{2+}$, $Ni^{3+}$, $Mn^{2+}$, $Mn^{3+}$, $Mn^{4+}$, $Mn^{6+}$, $Mn^{7+}$, $Co^{2+}$, $Co^{3+}$, $Cu^{2+}$, $Cd^{2+}$, $Fe^{2+}$, $Fe^{3+}$, and $Ti^{4+}$, for example, $Zn^{2+}$.

Optionally, the ZIF structure includes building units containing different metal ions, and is commonly referred to as mixed-metal ZIFs. For example, the ZIF structure includes a first building unit containing a first metal ion, such as $Zn^{2+}$, and a second building unit containing a second metal ion that is different from the first metal ion, such as $Cd^{2+}$, $Co^{2+}$, or $Ni^{2+}$; the assembly of the first and second building units forms the ZIF.

b. Imidazolate Linkers

The ZIF can include building units as shown in Formula (I), containing four imidazolate linkers $L_1$, $L_2$, $L_3$, and $L_4$. In ZIFs formed by the building units of Formula (I), the imidazolate linker coordinates to at least two metal ions. The imidazolate linker is neutral or has an overall negative charge. The imidazolate linkers participate in providing distance between these metal ions, resulting in a three-dimensional network of organic and inorganic components.

The ZIF structure can include building units containing a single type of imidazolate linker. For example, the ZIF structure includes building units of Formula (I), where $L_1$-$L_4$ are the same.

Optionally, the ZIF structure includes a group of building units, where the building units contain one or more different imidazolate linkers. For example, the ZIF structure includes a first building unit containing a first imidazolate linker, and a second building unit containing a second imidazolate linker that is different from the first imidazolate linker; the assembly of the first and second building units forms the ZIF. For example, the ZIF structure includes a first building unit of Formula (I) containing a first imidazolate linker, and a second building unit of Formula (I) containing a second imidazolate linker that is different from the first imidazolate linker; the assembly of the first and second building units forms the ZIF. In each of the first and second building units of Formula (I), $L_1$-$L_4$ are the same.

Optionally, at least one building unit forming the ZIF can contain different imidazolate linkers. For example, the ZIF structure includes at least one building unit that contains a first imidazolate linker and a second imidazolate linker that is different from the first imidazolate linker. For example, the ZIF structure includes at least one building unit of Formula (I), where at least one of $L_1$-$L_4$ is different from the others.

Optionally, the ZIF structure includes building units containing a single type of metal ion and a single type of imidazolate linker.

Optionally, the ZIF structure includes a group of building units containing different metal ions and/or imidazolate linkers. For example, the ZIF structure can include a first building unit containing a first metal ion and an imidazolate linker, and a second building unit containing a second metal ion and the same imidazolate linker, where the second metal ion is different from the first metal ion. For example, the ZIF structure can include a first building unit containing a metal ion and a first imidazolate linker, and a second building unit containing the same metal ion and a second imidazolate linker, where the second imidazolate linker is different from the first imidazolate linker. For example, the ZIF structure can include a first building unit containing a first metal ion and a first imidazolate linker, and a second building unit containing a second metal ion and a second imidazolate linker, where the second metal ion is different from the first metal ion, and the second imidazolate linker is different from the first imidazolate linker.

i. Linker Structures

The imidazolate linker can be an unmodified imidazole compound or a modified imidazole compound. Optionally, each of the imidazolate linker $L_1$, $L_2$, $L_3$, and $L_4$ can be represented by a general Formula (II) shown below:

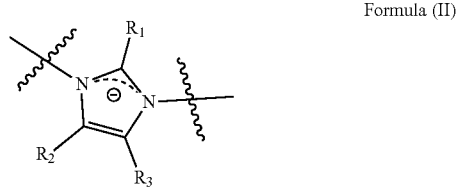

Formula (II)

wherein $R_1$, $R_2$, and $R_3$ are independently hydrogen, a substituted or unsubstituted alkyl, a substituted or unsubstituted alkenyl, a substituted or unsubstituted alkynyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a halogen, a hydroxyl, a substituted or unsubstituted alkoxy, an aroxy, a cyano, an isocyano, a nitro, a substituted or unsubstituted carbonyl, an amino, an amido, an azido, or a thiol, or $R_2$ and $R_3$ together form a substituted or unsubstituted cycloalkyl, a substituted or unsubstituted heterocyclyl, a substituted or unsubstituted aryl, or a substituted or unsubstituted heteroaryl;

wherein the substituents can be an unsubstituted alkyl, an unsubstituted alkenyl, an unsubstituted alkynyl, an unsubstituted heterocyclyl, an unsubstituted aryl, an unsubstituted heteroaryl, an unsubstituted polyaryl, an unsubstituted polyheteroaryl, an unsubstituted aralkyl, an unsubstituted carbonyl, an unsubstituted alkoxy, a halogen, a hydroxyl, a phenoxy, an aroxy, a cyano, an isocyano, a nitro, a carboxyl, an amino, an amido, an azido, an oxo, or a thiol, or a combination thereof.

Optionally, $R_1$, $R_2$, and $R_3$ are hydrogen (which is an "unmodified imidazole").

Optionally, $R_1$, $R_2$, and $R_3$ are independently hydrogen, a substituted or unsubstituted alkyl, a substituted or unsubstituted heterocyclyl, a substituted or unsubstituted aryl, a substituted or unsubstituted heteroaryl, a substituted or unsubstituted aralkyl, a halogen, a hydroxyl, a cyano, a nitro, an aldehyde, a carboxyl, an amino, or a thiol, or $R_2$ and $R_3$ together form a substituted or unsubstituted aryl or a substituted or unsubstituted heteroaryl; where the substituents can be a halogen, a hydroxyl, a cyano, a nitro, an aldehyde, a carboxyl, an amino, or a thiol, or a combination thereof.

The term "substituted" refers to moieties having one or more substituents replacing a hydrogen on one or more carbons of the hydrocarbon backbone.

The term "alkyl," as used herein, refers to the radical of saturated aliphatic groups. The alkyl for $R_1$, $R_2$, and $R_3$ of Formula (II) can be a linear alkyl, a branched alkyl, or a cyclic alkyl (either monocyclic or polycyclic; also referred herein as "cycloalkyl"). Exemplary alkyl include a linear $C_1$-$C_{30}$ alkyl, a branched $C_4$-$C_{30}$ alkyl, a cyclic $C_3$-$C_{30}$ alkyl, a linear $C_1$-$C_{20}$ alkyl, a branched $C_4$-$C_{20}$ alkyl, a cyclic $C_3$-$C_{20}$ alkyl, a linear $C_1$-$C_{10}$ alkyl, a branched $C_4$-$C_{10}$ alkyl, a cyclic $C_3$-$C_{10}$ alkyl, a linear $C_1$-$C_6$ alkyl, a branched $C_4$-$C_6$ alkyl, a cyclic $C_3$-$C_6$ alkyl, a linear $C_1$-$C_4$ alkyl, cyclic $C_3$-$C_4$ alkyl, such as a linear $C_1$-$C_{10}$, $C_1$-$C_9$, $C_1$-$C_8$, $C_1$-$C_7$, $C_1$-$C_6$, $C_1$-$C_5$, $C_1$-$C_4$, $C_1$-$C_3$, $C_1$-$C_2$ alkyl group, a branched $C_3$-$C_9$, $C_3$-$C_9$, $C_3$-$C_8$, $C_3$-$C_7$, $C_3$-$C_6$, $C_3$-$C_5$, $C_3$-$C_4$ alkyl group, or a cyclic $C_3$-$C_9$, $C_3$-$C_9$, $C_3$-$C_8$, $C_3$-$C_7$, $C_3$-$C_6$, $C_3$-$C_5$, $C_3$-$C_4$ alkyl group.

The term "alkenyl" as used herein is a hydrocarbon group of from 2 to 24 carbon atoms and structural formula containing at least one carbon-carbon double bond. The alkenyl for $R_1$, $R_2$, and $R_3$ of Formula (II) can be a linear alkenyl, a branched alkenyl, or a cyclic alkenyl (either monocyclic or polycyclic; also referred herein as "cycloalkenyl"). Exemplary alkenyl include a linear $C_1$-$C_{30}$ alkenyl, a branched $C_4$-$C_{30}$ alkenyl, a cyclic $C_3$-$C_{30}$ alkenyl, a linear $C_1$-$C_{20}$ alkenyl, a branched $C_4$-$C_{20}$ alkenyl, a cyclic $C_3$-$C_{20}$ alkenyl, a linear $C_1$-$C_{10}$ alkenyl, a branched $C_4$-$C_{10}$ alkenyl, a cyclic $C_3$-$C_{10}$ alkenyl, a linear $C_1$-$C_6$ alkenyl, a branched $C_4$-$C_6$ alkenyl, a cyclic $C_3$-$C_6$ alkenyl, a linear $C_1$-$C_4$ alkenyl, cyclic $C_3$-$C_4$ alkenyl, such as a linear $C_1$-$C_{10}$, $C_1$-$C_9$, $C_1$-$C_5$, $C_1$-$C_7$, $C_1$-$C_6$, $C_1$-$C_5$, $C_1$-$C_4$, $C_1$-$C_3$, $C_1$-$C_2$ alkenyl group, a branched $C_3$-$C_9$, $C_3$-$C_9$, $C_3$-$C_8$, $C_3$-$C_7$, $C_3$-$C_6$, $C_3$-$C_5$, $C_3$-$C_4$ alkenyl group, or a cyclic $C_3$-$C_9$, $C_3$-$C_9$, $C_3$-$C_8$, $C_3$-$C_7$, $C_3$-$C_6$, $C_3$-$C_5$, $C_3$-$C_4$ alkenyl group.

The term "alkynyl group" as used herein is a hydrocarbon group of 2 to 24 carbon atoms and a structural formula containing at least one carbon-carbon triple bond. The alkynyl for $R_1$, $R_2$, and $R_3$ of Formula (II) can be a linear alkynyl, a branched alkynyl, or a cyclic alkynyl (either monocyclic or polycyclic; also referred herein as "cycloalkynyl"). Exemplary alkynyl include a linear $C_1$-$C_{30}$ alkynyl, a branched $C_4$-$C_{30}$ alkynyl, a cyclic $C_3$-$C_{30}$ alkynyl, a linear $C_1$-$C_{20}$ alkynyl, a branched $C_4$-$C_{20}$ alkynyl, a cyclic $C_3$-$C_{20}$ alkynyl, a linear $C_1$-$C_{10}$ alkynyl, a branched $C_4$-$C_{10}$ alkynyl, a cyclic $C_3$-$C_{10}$ alkynyl, a linear $C_1$-$C_6$ alkynyl, a branched $C_4$-$C_6$ alkynyl, a cyclic $C_3$-$C_6$ alkynyl, a linear $C_1$-$C_4$ alkynyl, cyclic $C_3$-$C_4$ alkynyl, such as a linear $C_1$-$C_{10}$, $C_1$-$C_9$, $C_1$-$C_8$, $C_1$-$C_7$, $C_1$-$C_6$, $C_1$-$C_5$, $C_1$-$C_4$, $C_1$-$C_3$, $C_1$-$C_2$ alkynyl group, a branched $C_3$-$C_9$, $C_3$-$C_9$, $C_3$-$C_8$, $C_3$-$C_7$, $C_3$-$C_6$, $C_3$-$C_5$, $C_3$-$C_4$ alkynyl group, or a cyclic $C_3$-$C_9$, $C_3$-$C_9$, $C_3$-$C_8$, $C_3$-$C_7$, $C_3$-$C_6$, $C_3$-$C_5$, $C_3$-$C_4$ alkynyl group.

It is understood that any of the exemplary alkyl, alkenyl, and alkynyl groups for $R_1$, $R_2$, and $R_3$ of Formula (II) can be heteroalkyl, heteroalkenyl, and heteroalkynyl, respectively. "Heteroalkyl," "Heteroalkenyl," and "Heteroalkynyl," as used herein, refers to straight or branched chain, or cyclic carbon containing alkyl, alkenyl, or alkynyl radicals, or combinations thereof, containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized.

For example, the alkyl can be a linear $C_2$-$C_{30}$ heteroalkyl, a branched $C_4$-$C_{30}$ heteroalkyl, a cyclic $C_3$-$C_{30}$ heteroalkyl (i.e. a heterocycloalkyl), a linear $C_1$-$C_{20}$ heteroalkyl, a branched $C_4$-$C_{20}$ heteroalkyl, a cyclic $C_3$-$C_{20}$ heteroalkyl, a linear $C_1$-$C_{10}$ heteroalkyl, a branched $C_4$-$C_{10}$ heteroalkyl, a cyclic $C_3$-$C_{10}$ heteroalkyl, a linear $C_1$-$C_6$ heteroalkyl, a branched $C_4$-$C_6$ heteroalkyl, a cyclic $C_3$-$C_6$ heteroalkyl, a linear $C_1$-$C_4$ heteroalkyl, cyclic $C_3$-$C_4$ heteroalkyl, such as a linear $C_1$-$C_{10}$, $C_1$-$C_9$, $C_1$-$C_8$, $C_1$-$C_7$, $C_1$-$C_6$, $C_1$-$C_5$, $C_1$-$C_4$, $C_1$-$C_3$, $C_1$-$C_2$ heteroalkyl group, a branched $C_3$-$C_9$, $C_3$-$C_9$, $C_3$-$C_8$, $C_3$-$C_7$, $C_3$-$C_6$, $C_3$-$C_5$, $C_3$-$C_4$ heteroalkyl group, or a cyclic $C_3$-$C_9$, $C_3$-$C_9$, $C_3$-$C_8$, $C_3$-$C_7$, $C_3$-$C_6$, $C_3$-$C_5$, $C_3$-$C_4$ heteroalkyl group.

The alkenyl for $R_1$, $R_2$, and $R_3$ of Formula (II) can be a linear $C_2$-$C_{30}$ heteroalkenyl, a branched $C_4$-$C_{30}$ heteroalkenyl, a cyclic $C_3$-$C_{30}$ heteroalkenyl (i.e. a heterocycloalkenyl), a linear $C_1$-$C_{20}$ heteroalkenyl, a branched $C_4$-$C_{20}$ heteroalkenyl, a cyclic $C_3$-$C_{20}$ heteroalkenyl, a linear $C_1$-$C_{10}$ heteroalkenyl, a branched $C_4$-$C_{10}$ heteroalkenyl, a cyclic $C_3$-$C_{10}$ heteroalkenyl, a linear $C_1$-$C_6$ heteroalkenyl, a branched $C_4$-$C_6$ heteroalkenyl, a cyclic $C_3$-$C_6$ heteroalkenyl, a linear $C_1$-$C_4$ heteroalkenyl, cyclic $C_3$-$C_4$ heteroalkenyl, such as a linear $C_1$-$C_{10}$, $C_1$-$C_9$, $C_1$-$C_5$, $C_1$-$C_7$, $C_1$-$C_6$, $C_1$-$C_5$, $C_1$-$C_4$, $C_1$-$C_3$, $C_1$-$C_2$ heteroalkenyl group, a branched $C_3$-$C_9$, $C_3$-$C_9$, $C_3$-$C_8$, $C_3$-$C_7$, $C_3$-$C_6$, $C_3$-$C_5$, $C_3$-$C_4$ heteroalkenyl group, or a cyclic $C_3$-$C_9$, $C_3$-$C_9$, $C_3$-$C_8$, $C_3$-$C_7$, $C_3$-$C_6$, $C_3$-$C_5$, $C_3$-$C_4$ heteroalkenyl group.

The alkynyl for $R_1$, $R_2$, and $R_3$ of Formula (II) can be a linear $C_2$-$C_{30}$ heteroalkynyl, a branched $C_4$-$C_{30}$ heteroalkynyl, a cyclic $C_3$-$C_{30}$ heteroalkynyl (i.e. a heterocycloalkynyl), a linear $C_1$-$C_{20}$ heteroalkynyl, a branched $C_4$-$C_{20}$ heteroalkynyl, a cyclic $C_3$-$C_{20}$ heteroalkynyl, a linear $C_1$-$C_{10}$ heteroalkynyl, a branched $C_4$-$C_{10}$ heteroalkynyl, a cyclic $C_3$-$C_{10}$ heteroalkynyl, a linear $C_1$-$C_6$ heteroalkynyl, a branched $C_4$-$C_6$ heteroalkynyl, a cyclic $C_3$-$C_6$ heteroalkynyl, a linear $C_1$-$C_4$ heteroalkynyl, cyclic $C_3$-$C_4$ heteroalkynyl, such as a linear $C_1$-$C_{10}$, $C_1$-$C_9$, $C_1$-$C_5$, $C_1$-$C_7$, $C_1$-$C_6$, $C_1$-$C_5$, $C_1$-$C_4$, $C_1$-$C_3$, $C_1$-$C_2$ heteroalkynyl group, a branched $C_3$-$C_9$, $C_3$-$C_9$, $C_3$-$C_8$, $C_3$-$C_7$, $C_3$-$C_6$, $C_3$-$C_5$, $C_3$-$C_4$ heteroalkynyl group, or a cyclic $C_3$-$C_9$, $C_3$-$C_9$, $C_3$-$C_8$, $C_3$-$C_7$, $C_3$-$C_6$, $C_3$-$C_5$, $C_3$-$C_4$ heteroalkynyl group.

The aryl group for $R_1$, $R_2$, and $R_3$ of Formula (II) can be a $C_5$-$C_{30}$ aryl, a $C_5$-$C_{20}$ aryl, a $C_5$-$C_{12}$ aryl, a $C_5$-$C_{11}$ aryl, a $C_5$-$C_9$ aryl, a $C_6$-$C_{20}$ aryl, a $C_6$-$C_{12}$ aryl, a $C_6$-$C_{11}$ aryl, or a $C_6$-$C_9$ aryl. It is understood that the aryl can be a heteroaryl, such as a $C_5$-$C_{30}$ heteroaryl, a $C_5$-$C_{20}$ heteroaryl, a $C_5$-$C_{12}$ heteroaryl, a $C_5$-$C_{11}$ heteroaryl, a $C_5$-$C_9$ heteroaryl, a $C_6$-$C_{30}$ heteroaryl, a $C_6$-$C_{20}$ heteroaryl, a $C_6$-$C_{12}$ heteroaryl, a $C_6$-$C_{11}$ heteroaryl, or a $C_6$-$C_9$ heteroaryl. The polyaryl group can be a $C_{10}$-$C_{30}$ polyaryl, a $C_{10}$-$C_{20}$ polyaryl, a $C_{10}$-$C_{12}$ polyaryl, a $C_{10}$-$C_{11}$ polyaryl, or a $C_{12}$-$C_{20}$ polyaryl. It is understood that the aryl can be a polyheteroaryl, such as a $C_{10}$-$C_{30}$ polyheteroaryl, a $C_{10}$-$C_{20}$ polyheteroaryl, a $C_{10}$-$C_{12}$ polyheteroaryl, a $C_{10}$-$C_{11}$ polyheteroaryl, or a $C_{12}$-$C_{20}$ polyheteroaryl.

The term "aryl" as used herein refers to any $C_5$-$C_{26}$ carbon-based aromatic group, heteroaromatic, fused aromatic, or fused heteroaromatic. For example, "aryl," as used herein can include 5-, 6-, 7-, 8-, 9-, 10-, 14-, 18-, and 24-membered single-ring aromatic groups, including, but not limited to, benzene, naphthalene, anthracene, phenanthrene, chrysene, pyrene, corannulene, coronene, etc. "Aryl" further encompasses polycyclic ring systems having two or more cyclic rings in which two or more carbons are common to two adjoining rings (i.e., "fused aromatic rings"), wherein at least one of the rings is aromatic, e.g., the other cyclic ring or rings can be cycloalkyls, cycloalkenyls, cycloalkynyls, aryls and/or heterocycles. The aryl group can be substituted with one or more groups including, but not limited to, alkyl, alkynyl, alkenyl, aryl, halide, nitro, amino, ester, ketone, aldehyde, hydroxy, carboxylic acid, or alkoxy.

"Heterocyclyl" refers to a cyclic radical attached via a ring carbon or nitrogen atom of a non-aromatic monocyclic or polycyclic ring containing 3-30 ring atoms, 3-20 ring atoms, 3-10 ring atoms, or 5-6 ring atoms, where each ring contains carbon and one to four heteroatoms each selected from the group consisting of non-peroxide oxygen, sulfur, and N(Y) wherein Y is absent or is H, O, $C_1$-$C_{10}$ alkyl, phenyl or benzyl, and optionally containing 1-3 double bonds and optionally substituted with one or more substituents. Heterocyclyl are distinguished from heteroaryl by definition. Heterocycles can be a heterocycloalkyl, a heterocycloalkenyl, a heterocycloalkynyl, etc, such as piperazinyl, piperidinyl, piperidonyl, 4-piperidonyl, dihydrofuro[2,3 b]tetrahydrofuran, morpholinyl, piperazinyl, piperidinyl, piperidonyl, 4 piperidonyl, piperonyl, pyranyl, 2H-pyrrolyl, 4H-quinolizinyl, quinuclidinyl, tetrahydrofuranyl, 6H-1,2,5-thiadiazinyl. Heterocyclic groups can optionally be substituted with one or more substituents as described above for alkyl and aryl.

The term "heteroaryl" refers to $C_5$-$C_{30}$ membered aromatic, fused aromatic, biaromatic ring systems, or combinations thereof, in which one or more carbon atoms on one or more aromatic ring structures have been substituted with a heteroatom. Suitable heteroatoms include, but are not limited to, oxygen, sulfur, and nitrogen. "Heteroaryl," as used herein, includes 5-, 6-, 7-, 8-, 9-, 10-, 14-, 18-, and 24-membered single ring aromatic groups that may include from one to four heteroatoms, for example, pyrrole, furan, thiophene, imidazole, oxazole, thiazole, triazole, tetrazole, pyrazole, pyridine, pyrazine, pyridazine and pyrimidine, and the like. The heteroaryl group may also be referred to as "aryl heterocycles" or "heteroaromatics". "Heteroaryl" further encompasses polycyclic ring systems having two or more rings in which two or more carbons are common to two adjoining rings (i.e., "fused rings") wherein at least one of the rings is heteroaromatic, e.g., the other cyclic ring or rings can be cycloalkyls, cycloalkenyls, cycloalkynyls, aryls, heterocycles, or combinations thereof. Examples of heteroaryl rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, furanyl, furazanyl, imidazolidinyl, imidazolinyl, imidazolyl, 1H indazolyl, indolenyl, indolinyl, indolizinyl, indolyl, 3H indolyl, isatinoyl, isobenzofuranyl, isochromanyl, isoindazolyl, isoindolinyl, isoindolyl, isoquinolinyl, isothiazolyl, isoxazolyl, methylenedioxyphenyl, naphthyridinyl, octahydroisoquinolinyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, pteridinyl, purinyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, quinoxalinyl, tetrahydroisoquinolinyl, tetrahydroquinolinyl, tetrazolyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl.

The term "polyaryl" refers to a chemical moiety that includes two or more aryls, heteroaryls, and combinations thereof. The aryls, heteroaryls, and combinations thereof, are fused, or linked via a single bond, ether, ester, carbonyl, amide, sulfonyl, sulfonamide, alkyl, azo, and combinations thereof. For example, a "polyaryl" can be polycyclic ring systems having two or more cyclic rings in which two or more carbons are common to two adjoining rings (i.e., "fused aromatic rings"), wherein two or more of the rings are aromatic. When two or more heteroaryls are involved, the chemical moiety can be referred to as a "polyheteroaryl."

The term "aralkyl" as used herein is an aryl group or a heteroaryl group having an alkyl, alkynyl, or alkenyl group as described above attached to the aromatic group, such as an aryl, a heteroaryl, a polyaryl, or a polyheteroaryl. An example of an aralkyl group is a benzyl group. The terms "alkoxyl" or "alkoxy," "aroxy" or "aryloxy," generally describe compounds represented by the formula —OR$^v$, wherein R$^v$ includes, but is not limited to, a substituted or unsubstituted alkyl, a substituted or unsubstituted alkenyl, a substituted or unsubstituted alkynyl, a substituted or unsubstituted cycloalkyl, a substituted or unsubstituted heterocyclyl, a substituted or unsubstituted cycloalkenyl, a substituted or unsubstituted heterocycloalkenyl, a substituted or unsubstituted aryl, a substituted or unsubstituted heteroaryl, a substituted or unsubstituted polyaryl, a substituted or unsubstituted polyheteroaryl, a substituted or unsubstituted arylalkyl, a substituted or unsubstituted heteroalkyl, a substituted or unsubstituted alkylaryl, a substituted or unsubstituted alkylheteroaryl, a substituted or unsubstituted aralkyl, a substituted or unsubstituted carbonyl, a thiol, an amido, and an amino Exemplary alkoxyl groups include methoxy, ethoxy, propyloxy, tert-butoxy and the like. A "lower alkoxy" group is an alkoxy group containing from one to six carbon atoms. An "ether" is two functional groups covalently linked by an oxygen as described below. Accordingly, the substituent of an alkyl that renders that alkyl an ether is or resembles an alkoxyl, such as can be represented by one of —O-alkyl, —O-alkenyl, —O-alkynyl, —O-aryl, —O-heteroaryl, —O-polyaryl, —O-polyheteroaryl, —O-heterocyclyl, etc.

The terms "aroxy" and "aryloxy," as used interchangeably herein, are represented by —O-aryl or —O-heteroaryl, wherein aryl and heteroaryl are as described herein.

The term "amino" as used herein includes the group

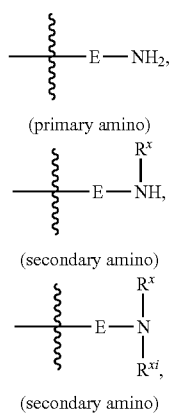

(primary amino)

(secondary amino)

(secondary amino)

-continued

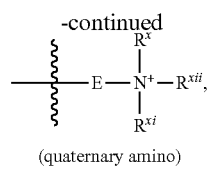

(quaternary amino)

wherein, E is absent, or E is substituted or unsubstituted alkyl, substituted or unsubstituted alkenyl, substituted or unsubstituted alkynyl, substituted or unsubstituted aralkyl, substituted or unsubstituted aryl, substituted or unsubstituted heteroaryl, a substituted or unsubstituted polyaryl, a substituted or unsubstituted polyheteroaryl, substituted or unsubstituted heterocyclyl, wherein independently of E, R$^x$, R$^{xi}$, and R$^{xii}$ each independently represent a substituted or unsubstituted alkyl, a substituted or unsubstituted alkenyl, a substituted or unsubstituted alkynyl, a substituted or unsubstituted carbonyl, a substituted or unsubstituted heterocyclyl, a substituted or unsubstituted aralkyl (e.g. a substituted or unsubstituted alkylaryl, a substituted or unsubstituted arylalkyl), a substituted or unsubstituted aryl, a substituted or unsubstituted heteroaryl, a substituted or unsubstituted polyaryl, a substituted or unsubstituted polyheteroaryl, a substituted or unsubstituted heterocyclyl, a hydroxyl, an alkoxy, a thiol, an amido, an amino, or —(CH$_2$)$_m$—R'''; R''' represents a hydroxyl group, a substituted or unsubstituted carbonyl group, a substituted or unsubstituted aryl, a substituted or unsubstituted cycloalkyl, a substituted or unsubstituted cycloalkenyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, an alkoxy, an amido, or an amino; and m is zero or an integer ranging from 1 to 8. The term "quaternary amino" also includes the groups where the nitrogen, R$^x$, R$^{xi}$, and R$^{xii}$ with the N$^+$ to which they are attached complete a heterocyclyl or heteroaryl having from 3 to 14 atoms in the ring structure.

The terms "amide" or "amido" are used interchangeably, refer to both "unsubstituted amido" and "substituted amido" and are represented by the general formula:

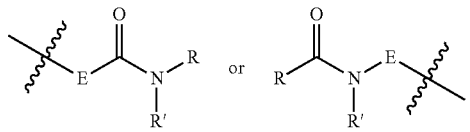

wherein, E is absent, or E is a substituted or unsubstituted alkyl, a substituted or unsubstituted alkenyl, a substituted or unsubstituted alkynyl, a substituted or unsubstituted aralkyl, a substituted or unsubstituted aryl, substituted or unsubstituted heteroaryl, a substituted or unsubstituted polyaryl, a substituted or unsubstituted polyheteroaryl, or a substituted or unsubstituted heterocyclyl, wherein independently of E, R and R' each independently represent a hydrogen, a substituted or unsubstituted alkyl, a substituted or unsubstituted alkenyl, a substituted or unsubstituted alkynyl, a substituted or unsubstituted carbonyl, a substituted or unsubstituted heterocyclyl, a substituted or unsubstituted aralkyl (e.g. a substituted or unsubstituted alkylaryl, a substituted or unsubstituted arylalkyl), a substituted or unsubstituted aryl, a substituted or unsubstituted heteroaryl, a substituted or unsubstituted polyaryl, a substituted or unsubstituted polyheteroaryl, a substituted or unsubstituted heterocyclyl, a hydroxyl, an alkoxy, a thiol, an amido, an amino, or —(CH$_2$)$_m$—R''', or R and R' taken together with the N atom to which they are attached complete a heterocycle having from 3 to 14 atoms in the ring structure; R''' represents a hydroxyl group, a substituted or unsubstituted carbonyl group, a substituted or unsubstituted aryl, a substituted or unsubstituted cycloalkyl, a substituted or unsubstituted cycloalkenyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, an azido, an alkoxy, an amido, or an amino; and m is zero or an integer ranging from 1 to 8. In some forms, when E is oxygen, a carbamate is formed.

"Carbonyl," as used herein, is art-recognized and includes such moieties as can be represented by the general formula:

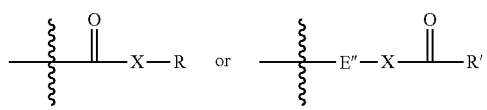

wherein X is a bond, or represents an oxygen or a sulfur, and R represents a hydrogen, a substituted or unsubstituted alkyl, a substituted or unsubstituted alkenyl, a substituted or unsubstituted alkynyl, a substituted or unsubstituted carbonyl, a substituted or unsubstituted heterocyclyl, a substituted or unsubstituted aralkyl (e.g. a substituted or unsubstituted alkylaryl, a substituted or unsubstituted arylalkyl), a substituted or unsubstituted aryl, a substituted or unsubstituted heteroaryl, a substituted or unsubstituted polyaryl, a substituted or unsubstituted polyheteroaryl, a substituted or unsubstituted heterocyclyl, a hydroxyl, an alkoxy, an azido, an amido, an amino, or —(CH$_2$)$_m$—R", or a pharmaceutical acceptable salt; E" is absent, or E" is substituted or unsubstituted alkyl, substituted or unsubstituted alkenyl, substituted or unsubstituted alkynyl, substituted or unsubstituted aralkyl, substituted or unsubstituted aryl, substituted or unsubstituted heteroaryl, a substituted or unsubstituted polyaryl, a substituted or unsubstituted polyheteroaryl, substituted or unsubstituted heterocyclyl; R' represents a hydrogen, a substituted or unsubstituted alkyl, a substituted or unsubstituted alkenyl, a substituted or unsubstituted alkynyl, a substituted or unsubstituted carbonyl, a substituted or unsubstituted heterocyclyl, a substituted or unsubstituted aralkyl (e.g. a substituted or unsubstituted alkylaryl, a substituted or unsubstituted arylalkyl), a substituted or unsubstituted aryl, a substituted or unsubstituted heteroaryl, a substituted or unsubstituted polyaryl, a substituted or unsubstituted polyheteroaryl, a substituted or unsubstituted heterocyclyl, a hydroxyl, an alkoxy, an amido, an amino, or —(CH$_2$)$_m$—R"; R" represents a hydroxyl group, a substituted or unsubstituted carbonyl group, a substituted or unsubstituted aryl, a substituted or unsubstituted cycloalkyl, a substituted or unsubstituted cycloalkenyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, an alkoxy, an amido, or an amino; and m is zero or an integer ranging from 1 to 8. Where X is oxygen and R is described as above, the moiety is also referred to as a carboxyl group. Where X is oxygen and R is hydrogen, the formula represents a "carboxylic acid". Where X is oxygen and R' is hydrogen, the formula represents a "formate". Where X is oxygen and R or R' is not hydrogen, the formula represents an "ester". In general, where the oxygen atom of the above formula is replaced by a sulfur atom, the formula represents a "thiocarbonyl" group. Where X is sulfur and R or R' is not hydrogen, the formula represents a "thioester". Where X is sulfur and R is hydrogen, the formula represents a "thiocarboxylic acid". Where X is sulfur and R' is hydrogen, the formula represents a "thioformate". Where X is a bond and R is not hydrogen, the above formula represents a "ketone". Where X is a bond and R is hydrogen, the above formula represents an "aldehyde".

The term "carboxyl" is as described above for carbonyl and is described more specifically by the formula —R$^{iv}$COOH, wherein R$^{iv}$ is a substituted or unsubstituted alkyl, a substituted or unsubstituted alkenyl, a substituted or unsubstituted alkynyl, a substituted or unsubstituted heterocyclyl, a substituted or unsubstituted alkylaryl, a substituted or unsubstituted arylalkyl, a substituted or unsubstituted aryl, a substituted or unsubstituted polyaryl, a substituted or unsubstituted polyheteroaryl, or a substituted or unsubstituted heteroaryl.

The term "phenoxy" refers to a compound of the formula —OR$^v$ wherein R$^v$ is (i.e., —O—C$_6$H$_5$). A phenoxy is a species of the aroxy genus.

The terms "thiol" are used interchangeably and are represented by —SR, where R can be a hydrogen, a sugar group, a substituted or unsubstituted alkyl, a substituted or unsubstituted alkenyl, a substituted or unsubstituted alkynyl, a substituted or unsubstituted heterocyclyl, a substituted or unsubstituted aryl, a substituted or unsubstituted heteroaryl, a substituted or unsubstituted aralkyl (e.g. a substituted or unsubstituted alkylaryl, a substituted or unsubstituted arylalkyl, etc.), a substituted or unsubstituted polyaryl, a substituted or unsubstituted polyheteroaryl, a substituted or unsubstituted carbonyl, an amido, an amino, an azido, an alkoxy, or an oxo, described above.

ii. Post-Framework Modification

When the imidazolate linker is a modified imidazole compound, the modification may be performed prior to ZIF assembly or following ZIF assembly (also referred herein as "post-framework functionalization").

For example, the imidazolate linker used to form the ZIF is a modified imidazole compound. Alternatively, the imidazolate linker used to form the ZIF is an unmodified imidazole compound, and the ZIF may be further modified with reacting with one or more post-framework reactants to introduce one or more functional group(s) as described above on the imidazolate linker. For example, the ZIF is formed by unmodified imidazole compounds and then further modified with one or more post-framework reactants to introduce amino, hydroxyl, thiol, aldehyde, or carboxyl, or a combination thereof on the imidazolate linker.

Methods and reactions for introducing functional groups on an unmodified imidazole compound, prior to ZIF assembly or post-framework functionalization, are known, such as those described in Bellina and Rossi, *Adv. Synth. Catal.*, 352:1223 (2010).

2. Targeting Ligands

The nanoparticles include a targeting ligand, optionally more than one targeting ligand, that targets a reproductive hormone or the receptor of a reproductive hormone. Typically, the targeting ligand is arranged on the outer surface of the cage such that it is exposed to the surrounding environment. The targeting ligand is directly attached to the outer surface of the cage and/or is conjugated to a surface modifying agent through which it attaches to the outer surface of the cage. For example, the targeting ligand is arranged on the outer surface of the ZIF such that it is exposed to the surrounding environment. The targeting ligand is directly attached to the outer surface of the ZIF and/or is conjugated to a surface modifying agent through which it attaches to the outer surface of the ZIF, as described below. The description below describes nanoparticles that contain a ZIF cage. However, these descriptions apply to other suitable materials for forming the cage, as well, such as those described above. Thus the references to a "ZIF" or "ZIF cage" herein also generally apply to other suitable materials for forming a cage.

Optionally, the targeting ligand is directly attached to the outer surface of the ZIF through an ionic bond, a covalent bond, a polar covalent bond, or Van Der Waal interactions, or a combination thereof. For example, the targeting ligand contains a chemical moiety containing one or more charges (negative charges or positive charges), such that it can ionically bind to the metal ions or the imidazolate linkers of the ZIFs and thereby attach to the outer surface of the ZIF.

Generally, the targeting ligand can bind to a receptor of a reproductive hormone, such as a receptor of gonadotropin-releasing hormone ("GnRH") or a receptor of Follicle-stimulating hormone ("FSH"). Bone loss and/or obesity in female mammals that occur during peri-/post-menopause are associated with high Follicle-stimulating hormone ("FSH") levels and low estrogen levels. GnRH is a releasing hormone that stimulates the production of FSH. By targeting reproductive hormones or their receptors the compositions and methods described herein are able to regulate hormones in a peri-/post-menopausal mammal, to prevent or reduce bone loss and/or obesity.

a. Exemplary Targeting Ligands

The nanoparticles include at least one of the following targeting ligands: a gonadotropin-releasing hormone ("GnRH") agonist or a follicle stimulating hormone ("FSH") receptor agonist, or a combination thereof. Optionally, the nanoparticles include one or more additional targeting ligands.

For example, the targeting ligand included in the nanoparticles is buserelin, azagly-naflorein, deslorelin, fertirelin, gonadorelin, goserelin, histrelin, lecirelin, leuprorelin, nafarelin, peforelin, peforelin acetate, triptorelin, leuprolide, leuprolide acetate, abarelix, cetorelix, degarelix, elagolix, ganirelix, linzagolix, relugolix, thiazolidinone compound 5, hexahydroquinoline derivative Org 214444-0, thienopyrimidine derivatives, such as thienopyrimidine derivative Org 43553, 5-amino-N-(tert-butyl)-4-(3-(isonicotinamido)phenyl)-2-(methylthio)thieno-[2,3-d]pyrimidine-6-carboxamide, 5-amino-N-(tert-butyl)-2-(methylthio)-4-(3-(thiophene-3-carboxamido)phenyl thieno[2,3-d]pyrimidine-6-carboxamide, 5-amino-N-(tert-butyl-2-(methylsulfonyl)-4-(3-(nicotinamido)phenyl)thieno[2,3-d]pyrimidine-6-carboxamide, 5-amino-N-(tert-butyl-4-(3-(1-methyl-1H-pyrazole-4-carboxamido)phenyl)-2-(methylsulfanyl)thieno[2,3-d]pyrimidine-6-carboxamide, 5-amino-N-(tert-butyl)-4-(3-(2-metoxynicotinamido)phenyl)-2-(methylthio)thieno[2,3-d]pyrimidine-6-carboxamide, 4-((3-(5-amino-6-(tert-butylcarbamoyl)-2-(methylthio)thieno[2,3-d]pyrimidine-4-il)phenyl)carbamoyl)pyridine 1-oxide, and 5-amino-N-(tert-butyl)-4-(3-(2-chloronicotinamido)phenyl)-2-(methylthio) thieno[2,3-d]pyrimidine-6-carboxamide; a diketopiperazine, or m-dihydropyridine, or a combination thereof.

In some embodiments, the targeting ligand included in the nanoparticles is buserelin.

3. Surface Modifying Agents a. Chemical Moiety for ZIF Attachment

The nanoparticles include a surface modifying agent, optionally more than one surface modifying agent, that attach to the outer surface of the cage. The surface modifying agent can attach to the outer surface of the cage through an ionic bond, a covalent bond, a polar covalent bond, or Van der Waals interactions, or a combination thereof. For example, the nanoparticles include a surface modifying agent, optionally more than one surface modifying agent, that attaches to the outer surface of the ZIF, where the surface modifying agent attaches to the outer surface of the ZIF through an ionic bond, a covalent bond, a polar covalent bond, or Van der Waals interactions, or a combination thereof. The description below describes nanoparticles that contain a ZIF cage. However, these descriptions apply to other suitable materials for forming the cage, as well, such as those described above. Thus the references to a "ZIF" or "ZIF cage" herein also generally apply to other suitable materials for forming a cage.

Optionally, the surface modifying agent attaches to the outer surface of the ZIF though an ionic bond. In these embodiments, the surface modifying agent may contain a chemical moiety containing one or more charges (positive charges or negative charges), such that it forms ionic bonding with the metal ions or the imidazolate linkers of the ZIF and thereby attaches to the outer surface of the ZIF. The charged chemical moiety can be on any suitable location of the surface modifying agent. For example, when the surface modifying agent is a polymer, the charged chemical moiety can be incorporated in any location in the backbone of the polymer, conjugated to one end or both ends of the polymer backbone, conjugated to the polymer backbone as a side group, or conjugated to a side chain of the polymer.

For example, the end of the surface modifying agent can contain a chemical moiety containing one or more charges (positive charges or negative charges), such that it forms ionic bonding with the metal ions or the imidazolate linkers of the ZIF and thereby attaches to the outer surface of the ZIF though the chemical moiety. For example, the end of the surface modifying agent contains a chemical moiety containing one or more negative charges, such that it forms ionic bonding with the metal ions of the ZIF and thereby attaches to the outer surface of the ZIF through the chemical moiety. For example, the end of the surface modifying agent contains a chemical moiety containing one or more positive charges, such that it ionically binds with one or more negative charges on the imidazolate linkers of the ZIF.

Optionally, the surface modifying agent itself contains one or more charges (positive charges or negative charges), such that it forms ionic bonds with the metal ions or the imidazolate linkers of the ZIF and thereby attaches to the outer surface of the ZIF though the chemical moiety. For example, the surface modifying agent contains a positively charged polyethylenimine backbone, such that if forms ionic bonding with the imidazolate linkers of the ZIF.

Examples of chemical moieties suitable to be incorporated in or conjugated to the surface modifying agent include, but are not limited to folate, L-methylfolate (5-MTHF), and glutamate, and a combination thereof.

b. Polymers

The surface modifying agent included in the nanoparticles can contain a polymer backbone. Any suitable polymer backbone can be used in forming the surface modifying agent of the nanoparticles. The polymer backbone can be hydrophobic or hydrophilic, or contain blocks that are hydrophobic and blocks that are hydrophilic. For example, the polymer backbone can be formed from hydrophobic monomers, hydrophilic monomers, or a combination of hydrophobic monomers and hydrophilic monomers.

Examples of suitable polymer backbones for forming the surface modifying agent include, but are not limited to, polyalkylene glycol, polylactic acid, polyglycolic acid, poly (lactic-co-glycolic acid), polyanhydrides, poly(ortho)esters, polyurethanes, poly(butyric acid), poly(valeric acid), poly (lactide-coaprolactone), and polyethylenimine, and a copolymer thereof.

For example, the polymer backbone of the surface modifying agent is polyethylene glycol.

The polymer backbone of the surface modifying agent may be unmodified or modified with one or more functional groups. The functional groups can be conjugated to the backbone of the polymer, conjugated to one end or both ends of the polymer backbone, or conjugated to a side chain of the polymer. For example, the polymer backbone of the surface modifying agent is modified to introduce one or more functional groups, such as amino, hydroxyl, thiol, aldehyde, or carboxyl, or a combination thereof. Surface modifying agents with functionalized polymer backbone are commercially available, for example, functionalized polyethylene glycols by Sigma Aldrich.

i. Molecular Weight

Generally, the polymer backbone of the surface modifying agent can have a molecular weight in a range from about 1 kDa to about 10 kDa. Optionally, the polymer backbone of the surface modifying agent can have a molecular weight in a range from about 2 kDa to about 10 kDa, from about 3 kDa to about 10 kDa, from about 4 kDa to about 10 kDa, from about 1 kDa to about 9 kDa, from about 2 kDa to about 9 kDa, from about 3 kDa to about 9 kDa, from about 4 kDa to about 9 kDa, from about 1 kDa to about 8 kDa, from about 2 kDa to about 8 kDa, from about 3 kDa to about 8 kDa, from about 4 kDa to about 8 kDa, from about 1 kDa to about 7 kDa, from about 2 kDa to about 7 kDa, from about 3 kDa to about 7 kDa, from about 4 kDa to about 7 kDa, from about 1 kDa to about 6 kDa, from about 2 kDa to about 6 kDa, from about 3 kDa to about 6 kDa, or from about 4 kDa to about 6 kDa.

For example, the polymer backbone of the surface modifying agent can have a molecular weight of about 5 kDa.

ii. Targeting Ligand Conjugation

Optionally, the surface modifying agent has a targeting ligand or more than one targeting ligand conjugated thereto. The targeting ligand may be conjugated to the backbone of the polymer, conjugated to one end of the polymer backbone, or conjugated to a side chain of the polymer, as long as the targeting ligand is exposed to the surrounding environment following nanoparticle assembly.

For example, the surface modifying agent has a first end that contains a charged chemical moiety, and a second end that is opposite to the first end and contains a targeting ligand conjugated thereto. In such embodiments, when the surface modifying agent is attached to the outer surface of the ZIF through the first end by ionic bonding, the second end containing the targeting ligand conjugated thereto is exposed to the surrounding environment.

Optionally, at least 20 wt % (weight of the surface modifying agent conjugated to the targeting ligand/total weight of the surface modifying agent attached to the cage) of the surface modifying agent is conjugated to the targeting ligand. For example, at least 20 wt % (weight of the surface modifying agent conjugated to the targeting ligand/total weight of the surface modifying agent attached to the ZIF) of the surface modifying agent is conjugated to the targeting ligand. For example, at least 25 wt %, at least 30 wt %, at least 35 wt %, at least 40 wt %, at least 45 wt %, at least 50 wt %, at least 55 wt %, at least 60 wt %, at least 65 wt %, at least 70 wt %, at least 75 wt %, at least 80 wt %, at least 85 wt %, at least 90 wt %, at least 95 wt %, in a range from 20 wt % to 100 wt %, from 30 wt % to 100 wt %, or from 40 wt % to 100 wt % of the surface modifying agent is conjugated to the targeting ligand.

4. Active Agents

The nanoparticles include an active agent, optionally more than one active agent, encapsulated in the cage. For example, the nanoparticles include an active agent, optionally more than one active agent, encapsulated in the ZIF. The active agents are generally able to reduce or prevent bone loss and/or obesity in the subject. Typically, the active agent can inactivate ribosomes of gonadotrophs, induce apoptosis of gonadotrophs, reduce or prevent secretion of FSH, and/or reduce the FSH level in a subject.

The description below describes nanoparticles that contain a ZIF cage. However, these descriptions apply to other suitable materials for forming the cage, as well. Thus the references to a "ZIF" or "ZIF cage" herein also generally apply to other suitable materials for forming a cage.

Optionally, the active agent encapsulated in the ZIF of the nanoparticles is a ribosome inactivating protein, an apoptosis inducer, a hormone, a receptor ligand, or a nucleic acid, or a combination thereof, that inactivates ribosomes of gonadotroph, reduce or prevent secretion of FSH, and/or reduce the FSH level in a peri-/post-menopausal of a subject.

Optionally, the active agent is stable when stored at 4° C. or room temperature for a period of time of at least 1 month, at least 6 months, at least 1 year, or up to 2 years. Optionally, the active agent is soluble in water and/or ethanol.

For example, the active agent encapsulated in the ZIF of the nanoparticles is a ribosome inactivating protein, such as saporin, gelonin, or a pokeweed antiviral protein ("PAP"), or a combination thereof. Other examples of ribosome inactivating proteins suitable for encapsulation in the ZIF include, but are not limited to, trichosanthin ("TCS"), bryodin, luffaculin, beta-luffin, a-momorcharin, cucurmosin, MAP30, b-momorcharin, GAP31, ricin, ebulin, abrus, mistletoe, bouganin, PD-$L_4$, dianthin, lychnin, MOD, charybdin, shiga, and cinnamomin, and a combination thereof.

For example, the active agent encapsulated in the ZIF structure of the nanoparticles is an apoptosis inducer, such as (±)-anatoxin A fumarate, actinomycin D, adriamycin, anisomycin, apoptosis activator 2, AT-101, betulinic acid, bioymifi, Bz 423, C75, camptothecin, carboplatin, chaetoglobosin A, cisplatin, clindamycin hydrochloride, cyclohexmide, 2,3,-DCPE hydrochloride, daptomycin, daunorubicin hydrochloride, doxorubicin hydrochloride, ellipticine, epirubicin hydrochloride, G 418 disulfate, gambogic acid, gedunin, hygromycin B, kaempferol, linezolid, mithramycin A, mitomycin C, MPC6827 hydrochloride, narciclasine, oncrasin 1, oxaliplatin, piperlongumine, puromycin dihydrochloride, rifampicin, rifaximin, SMBA 1, streptozotocin, temozolomide, tobramycin, triptolide, or trovafloxacin mesylate, or a combination thereof.

For example, more than one active agent is encapsulated in the ZIF structure of the nanoparticles, where a first active agent is a ribosome inactivating protein, such as any of the ribosome inactivating proteins described above, and a second active agent is an apoptosis inducer, such as any of the apoptosis inducers described above.

The nanoparticle can contain one or more active agents in a total concentration in the nanoparticle of at least about 0.00005 wt %, at least about 0.0001 wt %, at least about 0.0005 wt %, at least about 0.001 wt %, at least about 0.005 wt %, at least about 0.01 wt %, up to 10 wt %, up to 5 wt %, up to 1 wt %, up to 0.5 wt %, up to 0.1 wt %, in a range from about 0.00005 wt % to 10 wt %, from about 0.0001 wt % to 10 wt %, from about 0.0005 wt % to 10 wt %, from about 0.001 wt % to 10 wt %, from about 0.00005 wt % to 5 wt %, from about 0.0001 wt % to 5 wt %, from about 0.0005 wt % to 5 wt %, from about 0.001 wt % to 5 wt %, from about 0.00005 wt % to about 1 wt %, from about 0.0001 wt % to about 1 wt %, from about 0.0005 wt % to about 1 wt %, from about 0.001 wt % to 1 wt %, from about 0.00005 wt % to 0.5 wt %, from about 0.0001 wt % to 0.5 wt %, from about 0.0005 wt % to 0.5 wt %, from about 0.001 wt % to 0.5 wt %, from about 0.00005 wt % to about 0.1 wt %, from about 0.0001 wt % to about 0.1 wt %, from about 0.0005 wt % to about 0.1 wt %, from about 0.001 wt % to 0.1 wt %, from about 0.00005 wt % to 0.05 wt %, from about 0.0001 wt % to 0.05 wt %, from about 0.0005 wt % to 0.05 wt %, from about 0.001 wt % to 0.05 wt %, from about 0.00005 wt % to about 0.01 wt %, from about 0.0001 wt % to about 0.01 wt %, from about 0.0005 wt % to about 0.01 wt %, from about 0.001 wt % to 0.01 wt %, from about 0.00005 wt % to 0.005 wt %, from about 0.0001 wt % to 0.005 wt %, from about 0.0005 wt % to 0.005 wt %, from about 0.00005 wt % to about 0.001 wt %, from about 0.0001 wt % to about 0.001 wt %, or from about 0.0005 wt % to about 0.001 wt %, such as about 0.0006 wt %. The term "total concentration" with respect to the total concentration of the of one or more active agents in the nanoparticle refers to the sum of the weight of all of the active agent(s) encapsulated in a nanoparticle relative to the weight of the nanoparticle.

5. Optional Components

Optionally, the nanoparticles also include a diagnostic agent encapsulated in the cage. For example, the nanoparticles also include a diagnostic agent encapsulated in a ZIF. Any suitable diagnostic agent can be encapsulated in the cage of the nanoparticles. The encapsulation of the diagnostic agent allows visualization of the nanoparticles in vivo. Nanoparticles including a diagnostic agent are useful for imaging or assessing tissues of interest.

Exemplary diagnostic agents suitable to be encapsulated in the cage, such as the ZIF of the nanoparticles, include, but are not limited to, paramagnetic molecules, fluorescent/dye molecules, magnetic molecules, radionuclides, x-ray imaging agents, MRI imaging agents, ultrasound imaging agents, and contrast media.

For example, the nanoparticles includes a dye molecule encapsulated in the ZIF, such as Alexa Fluor 350, Alexa Fluor 405, Alexa Fluor 488, Alexa Fluor 532, Alexa Fluor 546, Alexa Fluor 555, Alexa Fluor 561, Alexa Fluor 568, Alexa Fluor 594, Alexa Fluor 647, Alexa Fluor 660, Alexa Fluor 680, Alexa Fluor 700, Alexa Fluor 750, pacific blue, coumarin, BODIPY FL, pacific green, oregon green, FITC, Cy3, pacific orange, PE-Cyanine7, PerCP-Cyanine5.5, TRITC, texas red, Cy5, eFLuor 450, eFluor 506, eFluor 660, PE-eFluor 610, PerCP-eFluor 710, APC-eFluor 780, super bright 436, super bright 600, super bright 645, super bright 702, super bright 780, DAPI, SYTOX green, SYTO 9, TO-PRO-3, propidium iodide, Qdot 525, Qdot 565, Qdot 605, Qdot 655, Qdot 705, Qdot 800, R-PE, APC, CFP, GFP, RFP, CF®350, CF®405S, CF®405M, CF®405L, CF®430, CF®440, CF®450, CF®488A, CF®503R, CF®514, CF®532, CF®535ST, CF®543, CF®550R, CF®555, CF®568, CF®570, CF®583, CF®583R, CF®594, CF®594ST, CF®620R, CF®633, CF®640R, CF®647, CF®660C, CF®660R, CF®680, CF®680R, CF®700, CF®750, CF®770, CF®790, CF®800, CF®820, or DyLight®649, or a combination thereof.

B. Properties

1. Surface Density of Surface Modifying Agents

Typically, the surface density of the surface modifying agent (also referred herein as "SMA") on the outer surface of the cage of the nanoparticles is sufficient to reduce non-specific protein adsorption in vivo. For example, the surface density of the SMA on the outer surface of the ZIF of the nanoparticles is sufficient to reduce non-specific protein adsorption in vivo. For example, the SMA has a surface density sufficient to achieve a brush configuration on the outer surface of the ZIF of the nanoparticles.

Optionally, the surface density of the SMA on the outer surface of the cage of the nanoparticles is at least 1 $SMA/nm^2$. For example, the surface density of the SMA on the outer surface of the cage of the nanoparticles is at least 2 $SMA/nm^2$, at least 3 $SMA/nm^2$, at least 4 $SMA/nm^2$, at least 5 $SMA/nm^2$, at least 7 $SMA/nm^2$, at least 10 $SMA/nm^2$, at least 15 $SMA/nm^2$, at least 20 $SMA/nm^2$, at least 25 $SMA/nm^2$, at least 30 $SMA/nm^2$, at least 35 $SMA/nm^2$, at least 40 $SMA/nm^2$, at least 45 $SMA/nm^2$, or at least 50 $SMA/nm^2$.

For example, the surface density of the SMA on the outer surface of the ZIF of the nanoparticles is at least 1 $SMA/nm^2$. For example, the surface density of the SMA on the outer surface of the ZIF of the nanoparticles is at least 2 $SMA/nm^2$, at least 3 $SMA/nm^2$, at least 4 $SMA/nm^2$, at least 5 $SMA/nm^2$, at least 7 $SMA/nm^2$, at least 10 $SMA/nm^2$, at least 15 $SMA/nm^2$, at least 20 $SMA/nm^2$, at least 25 $SMA/nm^2$, at least 30 $SMA/nm^2$, at least 35 $SMA/nm^2$, at least 40 $SMA/nm^2$, at least 45 $SMA/nm^2$, or at least 50 $SMA/nm^2$.

2. Nanoparticles Average Diameter

Typically, the nanoparticles have an average diameter (including the SMA) that is effective to increase nanoparticle circulation time and improve nanoparticle uptake by target cells.

Generally, the nanoparticles can have an average diameter (including the SMA) that is less than 100 nm and at least 10 nm. For example, the nanoparticles have an average diameter (including the SMA) in a range from about 10 nm to about 100 nm, from about 10 nm to about 90 nm, from about 10 nm to about 80 nm, from about 10 nm to about 70 nm, from about 10 nm to about 60 nm, from about 10 nm to about 50 nm, from about 20 nm to about 100 nm, from about 20 nm to about 90 nm, from about 20 nm to about 80 nm, from about 30 nm to about 100 nm, from about 30 nm to about 90 nm, or from about 30 nm to about 80 nm, such as in a range from about 10 nm to about 50 nm.

The average diameter of the nanoparticles can be determined using a standard technique, such as using scanning electron microscopy ("SEM") or using dynamic light scattering ("DLS").

For example, the nanoparticles have an average diameter (including the SMA) of less than 100 nm, or in a range from about 10 nm to about 100 nm, from about 10 nm to about 90 nm, from about 10 nm to about 80 nm, from about 20 nm to about 100 nm, from about 20 nm to about 90 nm, from about 20 nm to about 80 nm, from about 30 nm to about 100 nm, from about 30 nm to about 90 nm, or from about 30 nm to about 80 nm, measured by DLS.

II. Pharmaceutical Formulations

Pharmaceutical formulations that contain nanoparticles in a form suitable for administration to a mammal, and particularly for delivery to the pituitary and/or ovaries of the mammal, are disclosed. The pharmaceutical formulations may contain a plurality of the nanoparticles described herein. The nanoparticles in the plurality of nanoparticles may be formed from the same components or different components. For example, the nanoparticles in the plurality of nanoparticles contained in the pharmaceutical formulation are all the same, i.e. formed from the same cage, such as the same ZIF, same surface modifying agent, same targeting ligand, and same active agent. For example, one or more of the nanoparticles in the plurality of nanoparticles are formed from a cage, a surface modifying agent, a targeting ligand, and/or an active agent that is(are) different from the cage, surface modifying agent, targeting ligand, and/or active agent forming one or more of the other nanoparticles in the plurality of nanoparticles. For example, a first set of nanoparticles in the plurality of nanoparticles contained in the pharmaceutical formulation is formed from a first ZIF, a first surface modifying agent, a first targeting ligand, and a first active agent; and a second set of nanoparticles in the plurality of nanoparticles contained in the pharmaceutical formulation is formed from a second ZIF, a second surface modifying agent, a second targeting ligand, and a second active agent, where the first ZIF is the same or different from the second ZIF, the first surfacing modifying agent is the same or different from the second surface modifying agent, the first targeting ligand is the same or different from the second targeting ligand, and the first active agent is the same or different from the second active agent.

Typically, the active agent(s) in the pharmaceutical formulation is present in an amount effective to inactivate ribosomes of gonadotroph, induce apoptosis of gonadotrophs, reduce or prevent secretion of FSH, and/or reduce the FSH level in a peri-/post-menopausal mammal. Optionally, the active agent(s) in the pharmaceutical formulation is present in an amount effective to reduce the body weight, reduce the percentage of fat, and/or reduce the body mass index ("BMI") of the subject in the peri-/post-menopausal mammal.

The pharmaceutical formulation may include pharmaceutically acceptable carriers and/or one or more pharmaceutically acceptable excipients. For example, the pharmaceutical formulation may be in the form of a liquid, such as a solution or a suspension, and contain a plurality of the disclosed nanoparticles in an aqueous medium and, optionally, one or more suitable excipients for the liquid formulation. Optionally, the pharmaceutical formulation is in a solid form, and contains a plurality of the disclosed nanoparticles and one or more suitable excipients for a solid formulation. The solid formulation can be dissolved or suspended in a suitable carrier to form a liquid pharmaceutical formulation prior to use.

A. Carriers and Excipients

The pharmaceutical formulation contains one or more pharmaceutically acceptable carriers and/or excipients. Suitable pharmaceutically acceptable carriers and excipients are generally recognized as safe (GRAS), and may be administered to an individual without causing undesirable biological side effects or unwanted interactions.

Representative carriers and excipients include solvents (including buffers), diluents, pH modifying agents, preservatives, antioxidants, suspending agents, wetting agents, viscosity modifiers, tonicity agents, and stabilizing agents, and a combination thereof.

Nanoparticles for delivering active agents to the pituitary and/or ovaries of the mammal can be dissolved or suspended in a suitable carrier to form a liquid pharmaceutical formulation, such as sterile saline, phosphate buffered saline (PBS), balanced salt solution (BSS), viscous gel, or other pharmaceutically acceptable carriers for administration. The pharmaceutical formulation may also be a sterile solution, suspension, or emulsion in a nontoxic, parenterally acceptable diluent or solvent.

Excipients can be added to a liquid or solid pharmaceutical formulation to assist in sterility, stability (e.g. shelf-life), integration, and to adjust and/or maintain pH or isotonicity of the nanoparticles in the pharmaceutical formulation, such as diluents, pH modifying agents, preservatives, antioxidants, suspending agents, wetting agents, viscosity modifiers, tonicity agents, and stabilizing agents, and a combination thereof.

B. Form

The pharmaceutical formulation containing a plurality of the disclosed nanoparticles can be in a liquid form as a liquid formulation for parenteral administration (e.g. intramuscular administration, intravenous administration, intraperitoneal administration, and subcutaneous administration) to a subject. Optionally, the pharmaceutical formulation containing a plurality of the disclosed nanoparticles is in a solid form, which can be dissolved or suspended in a suitable carrier to form a liquid formulation for parenteral administration.

1. Parenteral Formulations

Optionally, the pharmaceutical formulation containing a plurality of the disclosed nanoparticles is in a form suitable for administration directly into the blood stream, into muscle, or into an internal organ. Suitable routes for such parenteral administration include intravenous, intraarterial, intraperitoneal, intrathecal, epidural, intracerebroventricular, intraurethral, intrasternal, intracranial, intramuscular, and subcutaneous delivery. Suitable means for parenteral administration include needle (including microneedle) injectors, needle-free injectors, and infusion techniques.

For example, the pharmaceutical formulation containing a plurality of the nanoparticles is in a form suitable for intramuscular administration, intravenous administration, intraperitoneal administration, or subcutaneous administration, or a combination thereof.

Parenteral formulations containing the nanoparticles described herein are typically aqueous solutions which can contain excipients such as salts, carbohydrates and buffering agents (e.g., from about pH 6.5 to about pH 8.0, from about pH 6.5 to about pH 7.4, from about pH 6.5 to about pH 7.0, from about pH 7.0 to pH 8.0, or from about pH 7.0 to about pH 7.4), but, for some applications, they may be more suitably formulated as a sterile aqueous solution or as a dried form to be used in conjunction with a suitable vehicle such as sterile, pyrogen-free water. The liquid formulations containing the nanoparticles for parenteral administration may be a solution, a suspension, or an emulsion.

The liquid pharmaceutically acceptable carrier forming the parenteral formulation containing the nanoparticles can include one or more physiologically compatible buffers, such as a phosphate buffers. One skilled in the art can readily determine a suitable saline content and pH for an aqueous carrier for administration (e.g., from pH 6.5 to about pH 8.0, from about pH 6.5 to about pH 7.4, from about pH 6.5 to about pH 7.0, from about pH 7.0 to pH 8.0, or from about pH 7.0 to about pH 7.4).

Liquid formulations containing the nanoparticles for parenteral administration may include one or more suspending agents, such as cellulose derivatives, sodium alginate, polyvinylpyrrolidone, gum tragacanth, or lecithin. The liquid formulations may also include one or more preservatives, such as ethyl or n-propyl p-hydroxybenzoate.

Optionally, the liquid formulation containing the nanoparticles contains one or more solvents that are low toxicity organic (i.e., nonaqueous) class 3 residual solvents, such as ethanol, acetone, ethyl acetate, tetrahydrofuran, ethyl ether, and propanol, and a combination thereof. Any such solvents included in the liquid formulation should not detrimentally react with the one or more active agents present in the nanoparticles in the liquid formulation. Solvents such as freon, alcohol, glycol, polyglycol, or fatty acid, can also be included in the liquid formulation containing the nanoparticles as desired to increase the volatility of the solution or suspension.

Liquid formulations containing the nanoparticles for parenteral administration may also contain minor amounts of polymers, surfactants, or other pharmaceutically acceptable excipients known to those in the art. In this context, "minor amounts" means an amount that is sufficiently small to avoid adversely affecting uptake of the nanoparticles by the targeted cells, such as pituitary gonadotrophs.

The preparation of parenteral formulations containing the nanoparticles is typically under sterile conditions, for example, by lyophilisation, which can be accomplished using standard pharmaceutical techniques known to those skilled in the art.

Formulations for parenteral administration containing the nanoparticles may be formulated to provide immediate and/or modified release of the active agent. Modified release formulations include delayed, sustained, pulsed, controlled, targeted and programmed release formulations.

C. Dosage/Wt % Concentration

The pharmaceutical formulation contains an effective amount of the active agent(s) encapsulated in the nanoparticles for preventing or reducing peri-/post-menopausal bone loss and/or obesity. Typically, the active agent(s) is present in the pharmaceutical formulation in an effective amount to reduce or prevent peri/post-menopausal bone loss and/or obesity. Typically, the amount of the active agent(s) in the pharmaceutical formulation is effective to inactivate ribosomes of gonadotroph, induce apoptosis of gonadotrophs, reduce or prevent secretion of FSH, and/or reduce the FSH levels in a subject, and thereby reduce or prevent peri/post-menopausal bone loss and/or obesity.

Optionally, the pharmaceutical formulation contains active agent(s) in an amount that is effective to reduce or prevent bone loss, reduce body weight, reduce percentage of fat, reduce BMI, and/or increase the leptin level in the blood of a peri-/post-menopausal mammal.

Optionally, the pharmaceutical formulation contains active agent(s) in an effective amount to reduce the body weight, reduce the percentage of fat, and/or reduce the BMI of the subject by at least 5%, at least 10%, at least 15%, at least 20%, at least 25%, or at least 30% compared to the body weight, the percentage of fat, and/or the BMI of the subject before treatment. Optionally, the pharmaceutical formulation contains active agent(s) in an effective amount to increase the leptin level in the blood of the subject by at least 5%, at least 10%, at least 15%, at least 20%, at least 25%, or at least 30% compared to the leptin level in the blood of the subject before treatment.

Optionally, the pharmaceutical formulation contains active agent(s) in an effective amount to reduce bone loss in the subject as shown by an increase/decrease of an osteoporosis biomarker level in the blood of the subject by at least 5%, at least 10%, at least 15%, at least 20%, at least 25%, or at least 30% compared to the osteoporosis biomarker level in the blood of the subject before treatment. Optionally, the pharmaceutical formulation contains active agent(s) in an effective amount to reduce bone loss in the subject as shown by an increase of the levels of one or more osteoporosis biomarkers in the blood of the subject by at least 5%, at least 10%, at least 15%, at least 20%, at least 25%, or at least 30% compared to the levels of the one or more osteoporosis biomarkers in the blood of the subject before treatment. Optionally, the pharmaceutical formulation contains active agent(s) in an effective amount to reduce bone loss in the subject as shown by a decrease of the levels of one or more osteoporosis biomarkers in the blood of the subject by at least 5%, at least 10%, at least 15%, at least 20%, at least 25%, or at least 30% compared to the levels of the one or more osteoporosis biomarkers in the blood of the subject before treatment.

Examples of osteoporosis biomarkers suitable for showing the reduction of bone loss in a subject include, but are not limited to, osteocalcin, bone specific alkaline phosphatase, PINP, PICP, NTX-1, TRAP5B, osteopontin, and bone sialoprotein, and a combination thereof.

For example, the pharmaceutical formulation contains active agent(s) in an effective amount to reduce bone loss in the subject as shown by an increase of the osteocalcin, bone specific alkaline phosphatase, PINP, and/or PICP level in the blood of the subject by at least 5%, at least 10%, at least 15%, at least 20%, at least 25%, or at least 30% compared to the osteocalcin, bone specific alkaline phosphatase, PINP, and/or PICP level in the blood of the subject before treatment. For example, the pharmaceutical formulation contains active agent(s) in an effective amount to reduce bone loss in the subject as shown by a decrease of the NTX-1, TRAP5B, osteopontin, and/or bone sialoprotein level in the blood of the subject by at least 5%, at least 10%, at least 15%, at least 20%, at least 25%, or at least 30% compared to the NTX-1, TRAP5B, osteopontin, and/or bone sialoprotein level in the blood of the subject before treatment.

Optionally, the pharmaceutical formulation contains nanoparticles in an effective amount to reduce the body weight, reduce the percentage of fat, and/or reduce the BMI of the subject by at least 5%, at least 10%, at least 15%, at least 20%, at least 25%, or at least 30% compared to the body weight, the percentage of fat, and/or the BMI of the subject before treatment. Optionally, the pharmaceutical formulation contains nanoparticles in an effective amount to increase the leptin level in the blood of the subject by at least 5%, at least 10%, at least 15%, at least 20%, at least 25%, or at least 30% compared to the leptin level in the blood of the subject before treatment. Optionally, the pharmaceutical formulation contains nanoparticles in an effective amount to reduce bone loss in the subject as shown by an increase/decrease of an osteoporosis biomarker level in the blood of the subject by at least 5%, at least 10%, at least 15%, at least 20%, at least 25%, or at least 30% compared to the osteoporosis biomarker level in the blood of the subject before treatment. Optionally, the pharmaceutical formulation contains nanoparticles in an effective amount to reduce bone loss in the subject as shown by an increase of the levels of one or more osteoporosis biomarkers in the blood of the subject by at least 5%, at least 10%, at least 15%, at least 20%, at least 25%, or at least 30% compared to the levels of the one or more osteoporosis biomarkers in the blood of the subject before treatment. Optionally, the pharmaceutical formulation contains nanoparticles in an effective amount to reduce bone loss in the subject as shown by a decrease of the level(s) of one or more osteoporosis biomarkers in the blood of the subject by at least 5%, at least 10%, at least 15%, at least 20%, at least 25%, or at least 30% compared to the level(s) of the one or more osteoporosis biomarkers in the blood of the subject before treatment.

The total concentration of the active agent(s) in the pharmaceutical formulation that is effective to inactivate ribosomes of gonadotroph, induce apoptosis of gonadotrophs, reduce or prevent secretion of follicle stimulating hormone, and/or reduce the FSH levels in a subject is typically in a range from about 0.000001 wt % to 20 wt %, from about 0.000005 wt % to 20 wt %, from about 0.00001 wt % to 20 wt %, from about 0.00005 wt % to 20 wt %, from about 0.0001 wt % to 20 wt %, from about 0.0005 wt % to 20 wt %, from about 0.001 wt % to 20 wt %, from about 0.000001 wt % to 10 wt %, from about 0.000005 wt % to 10 wt %, from about 0.00001 wt % to 10 wt %, from about 0.00005 wt % to 10 wt %, from about 0.0001 wt % to 10 wt %, from about 0.0005 wt % to 10 wt %, from about 0.001 wt % to 10 wt %, from about 0.000001 wt % to 5 wt %, from about 0.000005 wt % to 5 wt %, from about 0.00001 wt % to 5 wt %, from about 0.00005 wt % to 5 wt %, from about 0.0001 wt % to 5 wt %, from about 0.0005 wt % to 5 wt %, from about 0.001 wt % to 5 wt %, from about 0.000001 wt % to 2 wt %, from about 0.000005 wt % to 2 wt %, from about 0.00001 wt % to 2 wt %, from about 0.00005 wt % to 2 wt %, from about 0.0001 wt % to 2 wt %, from about 0.0005 wt % to 2 wt %, from about 0.001 wt % to 2 wt %, from about 0.000001 wt % to 0.5 wt %, from about 0.000005 wt % to 0.5 wt %, from about 0.00001 wt % to 0.5 wt %, from about 0.00005 wt % to 0.5 wt %, from about 0.0001 wt % to 0.5 wt %, from about 0.0005 wt % to 0.5 wt %, from about 0.001 wt % to 0.5 wt %, from about 0.000001 wt % to 0.2 wt %, from about 0.000005 wt % to 0.2 wt %, from about 0.00001 wt % to 0.2 wt %, from about 0.00005 wt % to 0.2 wt %, from about 0.0001 wt % to 0.2 wt %, from about 0.0005 wt % to 0.2 wt %, from about 0.001 wt % to 0.2 wt %, from about 0.000001 wt % to 0.05 wt %, from about 0.000005 wt % to 0.05 wt %, from about 0.00001 wt % to 0.05 wt %, from about 0.00005 wt % to 0.05 wt %, from about 0.0001 wt % to 0.05 wt %, from about 0.0005 wt % to 0.05 wt %, from about 0.001 wt % to 0.05 wt %, from about 0.000001 wt % to 0.02 wt %, from about 0.000005 wt % to 0.02 wt %, from about 0.00001 wt % to 0.02 wt %, from about 0.00005 wt % to 0.02 wt %, from about 0.0001 wt % to 0.02 wt %, from about 0.0005 wt % to 0.02 wt %, from about 0.001 wt % to 0.02 wt %, from about 0.000001 wt % to 0.005 wt %, from about 0.000005 wt % to 0.005 wt %, from about 0.00001 wt % to 0.005 wt %, from about 0.00005 wt % to 0.005 wt %, from about 0.0001 wt % to 0.005 wt %, from about 0.0005 wt % to 0.005 wt %, from about 0.000001 wt % to 0.002 wt %, from about 0.000005 wt % to 0.002 wt %, from about 0.00001 wt % to 0.002 wt %, from about 0.00005 wt % to 0.002 wt %, from about 0.0001 wt % to 0.002 wt %, or from about 0.0005 wt % to 0.002 wt %. The term "total concentration of the active agent(s) in the pharmaceutical formulation" refers to the sum of the weight of all active agent(s) encapsulated in the nanoparticles relative to the weight of the formulation.

The total concentration of the active agent(s) in the pharmaceutical formulation that is effective to prevent or reduce peri-/post-menopausal bone loss and/or obesity in the subject is typically in a range from about from about 0.000001 wt % to 20 wt %, from about 0.000005 wt % to 20 wt %, from about 0.00001 wt % to 20 wt %, from about 0.00005 wt % to 20 wt %, from about 0.0001 wt % to 20 wt %, from about 0.0005 wt % to 20 wt %, from about 0.001 wt % to 20 wt %, from about 0.000001 wt % to 10 wt %, from about 0.000005 wt % to 10 wt %, from about 0.00001 wt % to 10 wt %, from about 0.00005 wt % to 10 wt %, from about 0.0001 wt % to 10 wt %, from about 0.0005 wt % to 10 wt %, from about 0.001 wt % to 10 wt %, from about 0.000001 wt % to 5 wt %, from about 0.000005 wt % to 5 wt %, from about 0.00001 wt % to 5 wt %, from about 0.00005 wt % to 5 wt %, from about 0.0001 wt % to 5 wt %, from about 0.0005 wt % to 5 wt %, from about 0.001 wt % to 5 wt %, from about 0.000001 wt % to 2 wt %, from about 0.000005 wt % to 2 wt %, from about 0.00001 wt % to 2 wt %, from about 0.00005 wt % to 2 wt %, from about 0.0001 wt % to 2 wt %, from about 0.0005 wt % to 2 wt %, from about 0.001 wt % to 2 wt %, from about 0.000001 wt % to 0.5 wt %, from about 0.000005 wt % to 0.5 wt %, from about 0.00001 wt % to 0.5 wt %, from about 0.00005 wt % to 0.5 wt %, from about 0.0001 wt % to 0.5 wt %, from about 0.0005 wt % to 0.5 wt %, from about 0.001 wt % to 0.5 wt %, from about 0.000001 wt % to 0.2 wt %, from about 0.000005 wt % to 0.2 wt %, from about 0.00001 wt % to 0.2 wt %, from about 0.00005 wt % to 0.2 wt %, from about 0.0001 wt % to 0.2 wt %, from about 0.0005 wt % to 0.2 wt %, from about 0.001 wt % to 0.2 wt %, from about 0.000001 wt % to 0.05 wt %, from about 0.000005 wt % to 0.05 wt %, from about 0.00001 wt % to 0.05 wt %, from about 0.00005 wt % to 0.05 wt %, from about 0.0001 wt % to 0.05 wt %, from about 0.0005 wt % to 0.05 wt %, from about 0.001 wt % to 0.05 wt %, from about 0.000001 wt % to 0.02 wt %, from about 0.000005 wt % to 0.02 wt %, from about 0.00001 wt % to 0.02 wt %, from about 0.00005 wt % to 0.02 wt %, from about 0.0001 wt % to 0.02 wt %, from about 0.0005 wt % to 0.02 wt %, from about 0.001 wt % to 0.02 wt %, from about 0.000001 wt % to 0.005 wt %, from about 0.000005 wt % to 0.005 wt %, from about 0.00001 wt % to 0.005 wt %, from about 0.00005 wt % to 0.005 wt %, from about 0.0001 wt % to 0.005 wt %, from about 0.0005 wt % to 0.005 wt %, from about 0.000001 wt % to 0.002 wt %, from about 0.000005 wt % to 0.002 wt %, from about 0.00001 wt % to 0.002 wt %, from about 0.00005 wt % to 0.002 wt %, from about 0.0001 wt % to 0.002 wt %, or from about 0.0005 wt % to 0.002 wt %.

For example, the total concentration of the active agent(s) in the pharmaceutical formulation that is effective to reduce body weight, reduce percentage of fat, and/or reduce BMI of the subject by at least 5%, at least 10%, at least 15%, at least 20%, at least 25%, or at least 30% compared to the body weight, the percentage of fat, and/or the BMI of the subject before treatment is in a range from about 0.000001 wt % to 20 wt %, from about 0.000005 wt % to 20 wt %, from about 0.00001 wt % to 20 wt %, from about 0.00005 wt % to 20 wt %, from about 0.0001 wt % to 20 wt %, from about 0.0005 wt % to 20 wt %, from about 0.001 wt % to 20 wt %, from about 0.000001 wt % to 10 wt %, from about 0.000005 wt % to 10 wt %, from about 0.00001 wt % to 10 wt %, from about 0.00005 wt % to 10 wt %, from about 0.0001 wt % to 10 wt %, from about 0.0005 wt % to 10 wt %, from about 0.001 wt % to 10 wt %, from about 0.000001 wt % to 5 wt %, from about 0.000005 wt % to 5 wt %, from about 0.00001 wt % to 5 wt %, from about 0.00005 wt % to 5 wt %, from about 0.0001 wt % to 5 wt %, from about 0.0005 wt % to 5 wt %, from about 0.001 wt % to 5 wt %, from about 0.000001 wt % to 2 wt %, from about 0.000005 wt % to 2 wt %, from about 0.00001 wt % to 2 wt %, from about 0.00005 wt % to 2 wt %, from about 0.0001 wt % to 2 wt %, from about 0.0005 wt % to 2 wt %, from about 0.001 wt % to 2 wt %, from about 0.000001 wt % to 0.5 wt %, from about 0.000005 wt % to 0.5 wt %, from about 0.00001 wt % to 0.5 wt %, from about 0.00005 wt % to 0.5 wt %, from about 0.0001 wt % to 0.5 wt %, from about 0.0005 wt % to 0.5 wt %, from about 0.001 wt % to 0.5 wt %, from about 0.000001 wt % to 0.2 wt %, from about 0.000005 wt % to 0.2 wt %, from about 0.00001 wt % to 0.2 wt %, from about 0.00005 wt % to 0.2 wt %, from about 0.0001 wt % to 0.2 wt %, from about 0.0005 wt % to 0.2 wt %, from about 0.001 wt % to 0.2 wt %, from about 0.000001 wt % to 0.05 wt %, from about 0.000005 wt % to 0.05 wt %, from about 0.00001 wt % to 0.05 wt %, from about 0.00005 wt % to 0.05 wt %, from about 0.0001 wt % to 0.05 wt %, from about 0.0005 wt % to 0.05 wt %, from about 0.001 wt % to 0.05 wt %, from about 0.000001 wt % to 0.02 wt %, from about 0.000005 wt % to 0.02 wt %, from about 0.00001 wt % to 0.02 wt %, from about 0.00005 wt % to 0.02 wt %, from about 0.0001 wt % to 0.02 wt %, from about 0.0005 wt % to 0.02 wt %, from about 0.001 wt % to 0.02 wt %, from about 0.000001 wt % to 0.005 wt %, from about 0.000005 wt % to 0.005 wt %, from about 0.00001 wt % to 0.005 wt %, from about 0.00005 wt % to 0.005 wt %, from about 0.0001 wt % to 0.005 wt %, from about 0.0005 wt % to 0.005 wt %, from about 0.000001 wt % to 0.002 wt %, from about 0.000005 wt % to 0.002 wt %, from about 0.00001 wt % to 0.002 wt %, from about 0.00005 wt % to 0.002 wt %, from about 0.0001 wt % to 0.002 wt %, or from about 0.0005 wt % to 0.002 wt %.

For example, the total concentration of the active agent(s) in the pharmaceutical formulation that is effective to increase the leptin level in the blood of the subject by at least 5%, at least 10%, at least 15%, at least 20%, at least 25%, or at least 30% compared to the leptin level in the blood of the subject before treatment is in a range from about 0.000001 wt % to 20 wt %, from about 0.000005 wt % to 20 wt %, from about 0.00001 wt % to 20 wt %, from about 0.00005 wt % to 20 wt %, from about 0.0001 wt % to 20 wt %, from about 0.0005 wt % to 20 wt %, from about 0.001 wt % to 20 wt %, from about 0.000001 wt % to 10 wt %, from about 0.000005 wt % to 10 wt %, from about 0.00001 wt % to 10 wt %, from about 0.00005 wt % to 10 wt %, from about 0.0001 wt % to 10 wt %, from about 0.0005 wt % to 10 wt %, from about 0.001 wt % to 10 wt %, from about 0.000001 wt % to 5 wt %, from about 0.000005 wt % to 5 wt %, from about 0.00001 wt % to 5 wt %, from about 0.00005 wt % to 5 wt %, from about 0.0001 wt % to 5 wt %, from about 0.0005 wt % to 5 wt %, from about 0.001 wt % to 5 wt %, from about 0.000001 wt % to 2 wt %, from about 0.000005 wt % to 2 wt %, from about 0.00001 wt % to 2 wt %, from about 0.00005 wt % to 2 wt %, from about 0.0001 wt % to 2 wt %, from about 0.0005 wt % to 2 wt %, from about 0.001 wt % to 2 wt %, from about 0.000001 wt % to 0.5 wt %, from about 0.000005 wt % to 0.5 wt %, from about 0.00001 wt % to 0.5 wt %, from about 0.00005 wt % to 0.5 wt %, from about 0.0001 wt % to 0.5 wt %, from about 0.0005 wt % to 0.5 wt %, from about 0.001 wt % to 0.5 wt %, from about 0.000001 wt % to 0.2 wt %, from about 0.000005 wt % to 0.2 wt %, from about 0.00001 wt % to 0.2 wt %, from about 0.00005 wt % to 0.2 wt %, from about 0.0001 wt % to 0.2 wt %, from about 0.0005 wt % to 0.2 wt %, from about 0.001 wt % to 0.2 wt %, from about 0.000001 wt % to 0.05 wt %, from about 0.000005 wt % to 0.05 wt %, from about 0.00001 wt % to 0.05 wt %, from about 0.00005 wt % to 0.05 wt %, from about 0.0001 wt % to 0.05 wt %, from about 0.0005 wt % to 0.05 wt %, from about 0.001 wt % to 0.05 wt %, from about 0.000001 wt % to 0.02 wt %, from about 0.000005 wt % to 0.02 wt %, from about 0.00001 wt % to 0.02 wt %, from about 0.00005 wt % to 0.02 wt %, from about 0.0001 wt % to 0.02 wt %, from about 0.0005 wt % to 0.02 wt %, from about 0.001 wt % to 0.02 wt %, from about 0.000001 wt % to 0.005 wt %, from about 0.000005 wt % to 0.005 wt %, from about 0.00001 wt % to 0.005 wt %, from about 0.00005 wt % to 0.005 wt %, from about 0.0001 wt % to 0.005 wt %, from about 0.0005 wt % to 0.005 wt %, from about 0.000001 wt % to 0.002 wt %, from about 0.000005 wt % to 0.002 wt %, from about 0.00001 wt % to 0.002 wt %, from about 0.00005 wt % to 0.002 wt %, from about 0.0001 wt % to 0.002 wt %, or from about 0.0005 wt % to 0.002 wt %.

For example, the total concentration of the active agent(s) in the pharmaceutical formulation that is effective to reduce bone loss in the subject as shown by an increase/decrease of an osteoporosis biomarker level in the blood of the subject by at least 5%, at least 10%, at least 15%, at least 20%, at least 25%, or at least 30% compared to the osteoporosis biomarker level in the blood of the subject before treatment is in a range from about 0.000001 wt % to 20 wt %, from about 0.000005 wt % to 20 wt %, from about 0.00001 wt % to 20 wt %, from about 0.00005 wt % to 20 wt %, from about 0.0001 wt % to 20 wt %, from about 0.0005 wt % to 20 wt %, from about 0.001 wt % to 20 wt %, from about 0.000001 wt % to 10 wt %, from about 0.000005 wt % to 10 wt %, from about 0.00001 wt % to 10 wt %, from about 0.00005 wt % to 10 wt %, from about 0.0001 wt % to 10 wt %, from about 0.0005 wt % to 10 wt %, from about 0.001 wt % to 10 wt %, from about 0.000001 wt % to 5 wt %, from about 0.000005 wt % to 5 wt %, from about 0.00001 wt % to 5 wt %, from about 0.00005 wt % to 5 wt %, from about 0.0001 wt % to 5 wt %, from about 0.0005 wt % to 5 wt %, from about 0.001 wt % to 5 wt %, from about 0.000001 wt % to 2 wt %, from about 0.000005 wt % to 2 wt %, from about 0.00001 wt % to 2 wt %, from about 0.00005 wt % to 2 wt %, from about 0.0001 wt % to 2 wt %, from about 0.0005 wt % to 2 wt %, from about 0.001 wt % to 2 wt %, from about 0.000001 wt % to 0.5 wt %, from about 0.000005 wt % to 0.5 wt %, from about 0.00001 wt % to 0.5 wt %, from about 0.00005 wt % to 0.5 wt %, from about 0.0001 wt % to 0.5 wt %, from about 0.0005 wt % to 0.5 wt %, from about 0.001 wt % to 0.5 wt %, from about 0.000001 wt % to 0.2 wt %, from about 0.000005 wt % to 0.2 wt %, from about 0.00001 wt % to 0.2 wt %, from about 0.00005 wt % to 0.2 wt %, from about 0.0001 wt % to 0.2 wt %, from about 0.0005 wt % to 0.2 wt %, from about 0.001 wt % to 0.2 wt %, from about 0.000001 wt % to 0.05 wt %, from about 0.000005 wt % to 0.05 wt %, from about 0.00001 wt % to 0.05 wt %, from about 0.00005 wt % to 0.05 wt %, from about 0.0001 wt % to 0.05 wt %, from about 0.0005 wt % to 0.05 wt %, from about 0.001 wt % to 0.05 wt %, from about 0.000001 wt % to 0.02 wt %, from about 0.000005 wt % to 0.02 wt %, from about 0.00001 wt % to 0.02 wt %, from about 0.00005 wt % to 0.02 wt %, from about 0.0001 wt % to 0.02 wt %, from about 0.0005 wt % to 0.02 wt %, from about 0.001 wt % to 0.02 wt %, from about 0.000001 wt % to 0.005 wt %, from about 0.000005 wt % to 0.005 wt %, from about 0.00001 wt % to 0.005 wt %, from about 0.00005 wt % to 0.005 wt %, from about 0.0001 wt % to 0.005 wt %, from about 0.0005 wt % to 0.005 wt %, from about 0.000001 wt % to 0.002 wt %, from about 0.000005 wt % to 0.002 wt %, from about 0.00001 wt % to 0.002 wt %, from about 0.00005 wt % to 0.002 wt %, from about 0.0001 wt % to 0.002 wt %, or from about 0.0005 wt % to 0.002 wt %.

For example, the total concentration of the active agent(s) in the pharmaceutical formulation that is effective to reduce bone loss in the subject as shown by an increase of the levels of one or more osteoporosis biomarkers, such as osteocalcin, bone specific alkaline phosphatase, PINP, and/or PICP, in the blood of the subject by at least 5%, at least 10%, at least 15%, at least 20%, at least 25%, or at least 30% compared to the levels of the one or more osteoporosis biomarkers in the blood of the subject before treatment is in a range from about 0.000001 wt % to 20 wt %, from about 0.000005 wt % to 20 wt %, from about 0.00001 wt % to 20 wt %, from about 0.00005 wt % to 20 wt %, from about 0.0001 wt % to 20 wt %, from about 0.0005 wt % to 20 wt %, from about 0.001 wt % to 20 wt %, from about 0.00001 wt % to 10 wt %, from about 0.000005 wt % to 10 wt %, from about 0.00001 wt % to 10 wt %, from about 0.00005 wt % to 10 wt %, from about 0.0001 wt % to 10 wt %, from about 0.0005 wt % to 10 wt %, from about 0.001 wt % to 10 wt %, from about 0.000001 wt % to 5 wt %, from about 0.000005 wt % to 5 wt %, from about 0.00001 wt % to 5 wt %, from about 0.00005 wt % to 5 wt %, from about 0.0001 wt % to 5 wt %, from about 0.0005 wt % to 5 wt %, from about 0.001 wt % to 5 wt %, from about 0.000001 wt % to 2 wt %, from about 0.000005 wt % to 2 wt %, from about 0.00001 wt % to 2 wt %, from about 0.00005 wt % to 2 wt %, from about 0.0001 wt % to 2 wt %, from about 0.0005 wt % to 2 wt %, from about 0.001 wt % to 2 wt %, from about 0.000001 wt % to 0.5 wt %, from about 0.000005 wt % to 0.5 wt %, from about 0.00001 wt % to 0.5 wt %, from about 0.00005 wt % to 0.5 wt %, from about 0.0001 wt % to 0.5 wt %, from about 0.0005 wt % to 0.5 wt %, from about 0.001 wt % to 0.5 wt %, from about 0.000001 wt % to 0.2 wt %, from about 0.000005 wt % to 0.2 wt %, from about 0.00001 wt % to 0.2 wt %, from about 0.00005 wt % to 0.2 wt %, from about 0.0001 wt % to 0.2 wt %, from about 0.0005 wt % to 0.2 wt %, from about 0.001 wt % to 0.2 wt %, from about 0.000001 wt % to 0.05 wt %, from about 0.000005 wt % to 0.05 wt %, from about 0.00001 wt % to 0.05 wt %, from about 0.00005 wt % to 0.05 wt %, from about 0.0001 wt % to 0.05 wt %, from about 0.0005 wt % to 0.05 wt %, from about 0.001 wt % to 0.05 wt %, from about 0.000001 wt % to 0.02 wt %, from about 0.000005 wt % to 0.02 wt %, from about 0.00001 wt % to 0.02 wt %, from about 0.00005 wt % to 0.02 wt %, from about 0.0001 wt % to 0.02 wt %, from about 0.0005 wt % to 0.02 wt %, from about 0.001 wt % to 0.02 wt %, from about 0.000001 wt % to 0.005 wt %, from about 0.000005 wt % to 0.005 wt %, from about 0.00001 wt % to 0.005 wt %, from about 0.00005 wt % to 0.005 wt %, from about 0.0001 wt % to 0.005 wt %, from about 0.0005 wt % to 0.005 wt %, from about 0.000001 wt % to 0.002 wt %, from about 0.000005 wt % to 0.002 wt %, from about 0.00001 wt % to 0.002 wt %, from about 0.00005 wt % to 0.002 wt %, from about 0.0001 wt % to 0.002 wt %, or from about 0.0005 wt % to 0.002 wt %.

For example, the total concentration of the active agent(s) in the pharmaceutical formulation that is effective to reduce bone loss in the subject as shown by a decrease of the levels of one or more osteoporosis biomarkers, such as NTX-1, TRAP5B, osteopontin, and/or bone sialoprotein, in the blood of the subject by at least 5%, at least 10%, at least 15%, at least 20%, at least 25%, or at least 30% compared to the levels of the one or more osteoporosis biomarkers in the blood of the subject before treatment is in a range from about 0.000001 wt % to 20 wt %, from about 0.000005 wt % to 20 wt %, from about 0.00001 wt % to 20 wt %, from about 0.00005 wt % to 20 wt %, from about 0.0001 wt % to 20 wt %, from about 0.0005 wt % to 20 wt %, from about 0.001 wt % to 20 wt %, from about 0.000001 wt % to 10 wt %, from about 0.000005 wt % to 10 wt %, from about 0.00001 wt % to 10 wt %, from about 0.00005 wt % to 10 wt %, from about 0.0001 wt % to 10 wt %, from about 0.0005 wt % to 10 wt %, from about 0.001 wt % to 10 wt %, from about 0.000001 wt % to 5 wt %, from about 0.000005 wt % to 5 wt %, from about 0.00001 wt % to 5 wt %, from about 0.00005 wt % to 5 wt %, from about 0.0001 wt % to 5 wt %, from about 0.0005 wt % to 5 wt %, from about 0.001 wt % to 5 wt %, from about 0.000001 wt % to 2 wt %, from about 0.000005 wt % to 2 wt %, from about 0.00001 wt % to 2 wt %, from about 0.00005 wt % to 2 wt %, from about 0.0001 wt % to 2 wt %, from about 0.0005 wt % to 2 wt %, from about 0.001 wt % to 2 wt %, from about 0.000001 wt % to 0.5 wt %, from about 0.000005 wt % to 0.5 wt %, from about 0.00001 wt % to 0.5 wt %, from about 0.00005 wt % to 0.5 wt %, from about 0.0001 wt % to 0.5 wt %, from about 0.0005 wt % to 0.5 wt %, from about 0.001 wt % to 0.5 wt %, from about 0.000001 wt % to 0.2 wt %, from about 0.000005 wt % to 0.2 wt %, from about 0.00001 wt % to 0.2 wt %, from about 0.00005 wt % to 0.2 wt %, from about 0.0001 wt % to 0.2 wt %, from about 0.0005 wt % to 0.2 wt %, from about 0.001 wt % to 0.2 wt %, from about 0.000001 wt % to 0.05 wt %, from about 0.000005 wt % to 0.05 wt %, from about 0.00001 wt % to 0.05 wt %, from about 0.00005 wt % to 0.05 wt %, from about 0.0001 wt % to 0.05 wt %, from about 0.0005 wt % to 0.05 wt %, from about 0.001 wt % to 0.05 wt %, from about 0.000001 wt % to 0.02 wt %, from about 0.000005 wt % to 0.02 wt %, from about 0.00001 wt % to 0.02 wt %, from about 0.00005 wt % to 0.02 wt %, from about 0.0001 wt % to 0.02 wt %, from about 0.0005 wt % to 0.02 wt %, from about 0.001 wt % to 0.02 wt %, from about 0.000001 wt % to 0.005 wt %, from about 0.000005 wt % to 0.005 wt %, from about 0.00001 wt % to 0.005 wt %, from about 0.00005 wt % to 0.005 wt %, from about 0.0001 wt % to 0.005 wt %, from about 0.0005 wt % to 0.005 wt %, from about 0.000001 wt % to 0.002 wt %, from about 0.000005 wt % to 0.002 wt %, from about 0.00001 wt % to 0.002 wt %, from about 0.00005 wt % to 0.002 wt %, from about 0.0001 wt % to 0.002 wt %, or from about 0.0005 wt % to 0.002 wt %.

For example, the total concentration of the active agent(s) in the pharmaceutical formulation that is effective to reduce body weight, reduce percentage of fat, and/or reduce BMI of the subject by at least 5%, at least 10%, at least 15%, at least 20%, at least 25%, or at least 30% compared to the body weight, the percentage of fat, and/or the BMI of the subject before treatment; to increase the leptin level in the blood of the subject by at least 5%, at least 10%, at least 15%, at least 20%, at least 25%, or at least 30% compared to the leptin level in the blood of the subject before treatment; and to reduce bone loss in the subject as shown by an increase/decrease of an osteoporosis biomarker level in the blood of the subject by at least 5%, at least 10%, at least 15%, at least 20%, at least 25%, or at least 30% compared to the osteoporosis biomarker level in the blood of the subject before treatment is in a range from about 0.000001 wt % to 20 wt %, from about 0.000005 wt % to 20 wt %, from about 0.00001 wt % to 20 wt %, from about 0.00005 wt % to 20 wt %, from about 0.0001 wt % to 20 wt %, from about 0.0005 wt % to 20 wt %, from about 0.001 wt % to 20 wt %, from about 0.000001 wt % to 10 wt %, from about 0.000005 wt % to 10 wt %, from about 0.00001 wt % to 10 wt %, from about 0.00005 wt % to 10 wt %, from about 0.0001 wt % to 10 wt %, from about 0.0005 wt % to 10 wt %, from about 0.001 wt % to 10 wt %, from about 0.000001 wt % to 5 wt %, from about 0.000005 wt % to 5 wt %, from about 0.00001 wt % to 5 wt %, from about 0.00005 wt % to 5 wt %, from about 0.0001 wt % to 5 wt %, from about 0.0005 wt % to 5 wt %, from about 0.001 wt % to 5 wt %, from about 0.000001 wt % to 2 wt %, from about 0.000005 wt % to 2 wt %, from about 0.00001 wt % to 2 wt %, from about 0.00005 wt % to 2 wt %, from about 0.0001 wt % to 2 wt %, from about 0.0005 wt % to 2 wt %, from about 0.001 wt % to 2 wt %, from about 0.000001 wt % to 0.5 wt %, from about 0.000005 wt % to 0.5 wt %, from about 0.00001 wt % to 0.5 wt %, from about 0.00005 wt % to 0.5 wt %, from about 0.0001 wt % to 0.5 wt %, from about 0.0005 wt % to 0.5 wt %, from about 0.001 wt % to 0.5 wt %, from about 0.000001 wt % to 0.2 wt %, from about 0.000005 wt % to 0.2 wt %, from about 0.00001 wt % to 0.2 wt %, from about 0.00005 wt % to 0.2 wt %, from about 0.0001 wt % to 0.2 wt %, from about 0.0005 wt % to 0.2 wt %, from about 0.001 wt % to 0.2 wt %, from about 0.000001 wt % to 0.05 wt %, from about 0.000005 wt % to 0.05 wt %, from about 0.00001 wt % to 0.05 wt %, from about 0.00005 wt % to 0.05 wt %, from about 0.0001 wt % to 0.05 wt %, from about 0.0005 wt % to 0.05 wt %, from about 0.001 wt % to 0.05 wt %, from about 0.000001 wt % to 0.02 wt %, from about 0.000005 wt % to 0.02 wt %, from about 0.00001 wt % to 0.02 wt %, from about 0.00005 wt % to 0.02 wt %, from about 0.0001 wt % to 0.02 wt %, from about 0.0005 wt % to 0.02 wt %, from about 0.001 wt % to 0.02 wt %, from about 0.000001 wt % to 0.005 wt %, from about 0.000005 wt % to 0.005 wt %, from about 0.00001 wt % to 0.005 wt %, from about 0.00005 wt % to 0.005 wt %, from about 0.0001 wt % to 0.005 wt %, from about 0.0005 wt % to 0.005 wt %, from about 0.000001 wt % to 0.002 wt %, from about 0.000005 wt % to 0.002 wt %, from about 0.00001 wt % to 0.002 wt %, from about 0.00005 wt % to 0.002 wt %, from about 0.0001 wt % to 0.002 wt %, or from about 0.0005 wt % to 0.002 wt %.

The pharmaceutical formulation containing a plurality of the nanoparticles is optionally provided in a unit dosage form. The dosage of the nanoparticles in the pharmaceutical formulation in the unit dosage form can be in a range from about 0.01 mg to about 100 mg, from about 0.01 mg to about 90 mg, from about 0.01 mg to about 80 mg, from about 0.01 mg to about 60 mg, from about 0.01 mg to about 50 mg, from about 0.01 mg to about 30 mg, from about 0.01 mg to about 20 mg, from about 0.01 mg to about 10 mg, from about 0.1 mg to about 100 mg, from about 0.2 mg to about 100 mg, from about 0.3 mg to about 100 mg, from about 0.5 mg to about 100 mg, from about 1 mg to about 100 mg, from about 0.3 mg to about 90 mg, from about 0.3 mg to about 80 mg, from about 0.3 mg to about 60 mg, from about 0.3 mg to about 50 mg, from about 0.3 mg to about 30 mg, from about 0.2 mg to about 20 mg, or from about 0.1 mg to about 10 mg.

The pharmaceutical formulation containing a plurality of the nanoparticles is optionally provided in a unit dosage form. The dosage of the active agents in the pharmaceutical formulation in the unit dosage form can be in a range from about $5 \times 10^{-5}$ µg to about 0.5 µg, from about $5 \times 10^{-5}$ µg to about 0.1 µg, from about $5 \times 10^{-5}$ µg to about 0.01 µg, from about $5 \times 10^{-5}$ µg to about 0.005 µg, from about $5 \times 10^{-5}$ µg to about 0.001 µg, from about $5 \times 10^{-5}$ µg to about $5 \times 10^{-4}$ µg, from about $1 \times 10^{-4}$ µg to about 0.5 µg, from about $5 \times 10^{-4}$ µg to about 0.5 µg, from about 0.001 µg to about 0.5 µg, or from about 0.01 µg to about 0.5 µg.

III. Methods of Using the Nanoparticles

A. Preventing or Reducing Peri-/Post-Menopausal Bone Loss and/or Obesity

Methods for preventing or reducing peri-/post-menopausal bone loss and/or obesity in a subject using the nanoparticles are disclosed.

Generally, the method for preventing or reducing peri-/post-menopausal bone loss and/or obesity in a subject in need thereof includes administering to the subject a pharmaceutical formulation containing a plurality of the nanoparticles described above. The pharmaceutical formulation is administered in an effective amount to reduce or prevent bone loss, reduce body weight, reduce percentage of fat, reduce BMI, and/or increase the leptin level in the blood of the subject. For example, the pharmaceutical formulation administered is in an amount effective to reduce body weight, reduce percentage of fat, and/or reduce BMI of the subject. For example, the pharmaceutical formulation administered is in an amount effective to increase the leptin level in the blood of the subject. For example, the pharmaceutical formulation administered is in an amount effective to reduce bone loss in the subject as shown by an increase/decrease of an osteoporosis biomarker level in the blood of the subject.

The step of administering an effective amount of the pharmaceutical formulation can be achieved in a single administration step or using multiple steps of administering the pharmaceutical formulation.

The subject can be a peri-/post-menopausal mammal, such as a woman, a female dog, a female cat, a female rat, a female monkey, female rabbits, female guinea pigs, etc., that is in need of preventing and/or reducing bone loss and/or obesity.

The pharmaceutical formulation containing a plurality of the nanoparticles can be administered by intramuscular administration, intravenous administration, intraperitoneal administration, or subcutaneous administration, or a combination thereof.

1. Administering an Effective Amount of the Pharmaceutical Formulation

The step of administering an effective amount of the pharmaceutical formulation can be achieved in a single administration step or using multiple steps of administering the pharmaceutical formulation. Optionally the step of administering the pharmaceutical formulation is repeated more than one time, and following all of the steps of administering the formulation, an effective amount of the formulation is administered. For example, if the unit dosage form contains an effective amount of the active agent(s) to reduce or prevent bone loss, reduce body weight, reduce percentage of fat, reduce BMI, and/or increase the leptin level in the blood of the subject, then method only requires a single administration step. Alternatively, if the unit dosage form contains less than the required effective amount of the active agent(s) to reduce or prevent bone loss, reduce body weight, reduce percentage of fat, reduce BMI, and/or increase the leptin level in the blood of the subject, then the method involves at least two steps of administering the pharmaceutical formulation, and optionally more than two steps of administering the pharmaceutical formulation to the subject until an effective amount of the pharmaceutical formulation is administered to the subject to reduce or prevent bone loss, reduce body weight, reduce percentage of fat, reduce BMI, and/or increase the leptin level in the blood of the subject. When multiple administration steps are needed to administer an effective amount of the pharmaceutical formulation to the patient, each administration step may involve administering the same dosage or different dosages of the pharmaceutical formulation to the patient. In a preferred embodiment, the method involves a single administration of the pharmaceutical formulation in an effective amount to reduce or prevent bone loss, reduce body weight, reduce percentage of fat, reduce BMI, and/or increase the leptin level in the blood of the subject.

When multiple administration steps are needed to administer an effective amount of the pharmaceutical formulation to the patient, the administration steps may be performed regularly or irregularly. For example, the administration steps are performed at a suitable frequency, such as every hour, every 2 hours, every 5 hours, every 8 hours, every day, every 2 days, every 3 days, every 5 days, every 7 days, every 10 days, every two weeks, or every month. For example, the administration step is performed every hour, every 2 hours, every 5 hours, every 8 hours, every day, every 2 days, every 3 days, every 5 days, every 7 days, every 10 days, every two weeks, or every month for a period between one day and 6 months, between one day and 3 months, between one and thirty days, between one and ten days, between one and three days, between one and two days, or during one day. Alternatively, the administration may be performed irregularly, for example, the administration step is performed 1 day after the first administration, then 2 days after the second administration, then 5 days after the third administration, then 7 day after the fourth administration, and then 30 days after the fifth administration. The time interval between administrations are determined based on the patient's needs.

The pharmaceutical formulation is administered to the subject in an amount effective to inactivate ribosomes of gonadotroph, induce apoptosis of gonadotrophs, reduce or prevent secretion of follicle stimulating hormone, and/or reduce the FSH levels in the subject, and thereby prevent or reduce peri-/post-menopausal bone loss and/or obesity, optionally without significant side effects, such as increased blood pressure, anxiety or other behavioral disorders, increased risk of breast cancer, gastrointestinal side effects, such as nausea and diarrhea, reduced absorption of fat soluble vitamins, acute kidney injury in diabetic patients, and neuropsychiatric effects.

Optionally, the pharmaceutical formulation is administered to the subject in an effective amount to reduce or prevent bone loss in the subject. Optionally, the pharmaceutical formulation is administered to the subject in an effective amount to reduce body weight, reduce percentage of fat, and/or reduce BMI of the subject. Optionally, the pharmaceutical formulation is administered to the subject in an effective amount to increase the leptin level in the blood of the subject. Optionally, the pharmaceutical formulation is administered to the subject in an effective amount to reduce or prevent bone loss, reduce body weight, reduce percentage of fat, reduce BMI, and increase the leptin level in the blood of the subject. Optionally, the pharmaceutical formulation is administered to the subject in an effective amount to reduce or prevent bone loss, reduce body weight, reduce percentage of fat, reduce BMI, and/or increase the leptin level in the blood of the subject, without one or more significant side effects, such as increased blood pressure, anxiety and other behavioral disorders, increased risk of breast cancer, gastrointestinal side effects, such as nausea and diarrhea, reduced absorption of fat soluble vitamins, acute kidney injury in diabetic patients, and neuropsychiatric effects.

For example, the pharmaceutical formulation is administered to the subject in an effective amount to reduce bone loss in the subject as shown by an increase/decrease of an osteoporosis biomarker level in the blood of the subject compared to the leptin level in the blood of the subject before treatment, where the increase/decrease of the osteoporosis biomarker level in the blood of the subject occurs within about 14 days, within about 1 month, within about 3 months, or within about 6 months following the step of administration of the pharmaceutical formulation.

For example, the pharmaceutical formulation is administered to the subject in an effective amount to reduce bone loss in the subject as shown by an increase/decrease of an osteoporosis biomarker level in the blood of the subject by at least 5%, at least 10%, at least 15%, at least 20%, at least 25%, or at least 30% compared to the osteoporosis biomarker level in the blood of the subject before treatment, where the increase/decrease of the osteoporosis biomarker level in the blood of the subject occurs within about 14 days, within about 1 month, within about 3 months, or within about 6 months following administration of the pharmaceutical formulation.

For example, the pharmaceutical formulation is administered to the subject in an effective amount to reduce bone loss in the subject as shown by an increase of the osteocalcin, bone specific alkaline phosphatase, PINP, and/or PICP level in the blood of the subject by at least 5%, at least 10%, at least 15%, at least 20%, at least 25%, or at least 30% compared to the osteocalcin, bone specific alkaline phosphatase, PINP, and/or PICP level in the blood of the subject before treatment, where the increase of the osteocalcin, bone specific alkaline phosphatase, PINP, and/or PICP level in the blood of the subject occurs within about 14 days, within about 1 month, within about 3 months, or within about 6 months following administration of the pharmaceutical formulation.

For example, the pharmaceutical formulation is administered to the subject in an effective amount to reduce bone loss in the subject as shown by a decrease of the NTX-1, TRAP5B, osteopontin, and/or bone sialoprotein level in the blood of the subject by at least 5%, at least 10%, at least 15%, at least 20%, at least 25%, or at least 30% compared to the NTX-1, TRAP5B, osteopontin, and/or bone sialoprotein level in the blood of the subject before treatment, where the decrease of the NTX-1, TRAP5B, osteopontin, and/or bone sialoprotein level in the blood of the subject occurs within about 14 days, within about 1 month, within about 3 months, or within about 6 months following administration of the pharmaceutical formulation.

For example, the pharmaceutical formulation is administered to the subject in an effective amount to reduce the body weight, reduce the percentage of fat, and/or reduce the BMI of the subject compared to the body weight, the percentage of fat, and/or the BMI of the subject before treatment, where the reduction of the body weight, the percentage of fat, and/or the BMI of the subject occurs within about 14 days, within about 1 month, within about 3 months, or within about 6 months following administration of the pharmaceutical formulation.

For example, the pharmaceutical formulation is administered to the subject in an effective amount to reduce the body weight, reduce the percentage of fat, and/or reduce the BMI of the subject by at least 5%, at least 10%, at least 15%, at least 20%, at least 25%, or at least 30% compared to the body weight, the percentage of fat, and/or the BMI of the subject before treatment, where the reduction of the body weight, the percentage of fat, and/or the BMI of the subject occurs within about 14 days, within about 1 month, within about 3 months, or within about 6 months following administration of the pharmaceutical formulation.

For example, the pharmaceutical formulation is administered to the subject in an effective amount to increase the leptin level in the blood of the subject compared to the leptin level in the blood of the subject before treatment, where the increase of the leptin level in the blood of the subject occurs within about 14 days, within about 1 month, within about 3 months, or within about 6 months following administration of the pharmaceutical formulation.

For example, the pharmaceutical formulation is administered to the subject in an effective amount to increase the leptin level in the blood of the subject by at least 5%, at least 10%, at least 15%, at least 20%, at least 25%, or at least 30% compared to the leptin level in the blood of the subject before treatment, where the increase of the leptin level in the blood of the subject occurs within about 14 days, within about 1 month, within about 3 months, or within about 6 months following administration of the pharmaceutical formulation.

For example, the pharmaceutical formulation is administered to the subject in an effective amount to reduce bone loss in the subject as shown by an increase/decrease of an osteoporosis biomarker level in the blood of the subject compared to the osteoporosis biomarker level in the blood of the subject before treatment; to reduce the body weight, reduce the percentage of fat, and/or reduce the BMI of the subject compared to the body weight, the percentage of fat, and/or the BMI of the subject before treatment; and to increase the leptin level in the blood of the subject compared to the leptin level in the blood of subject before treatment within about 14 days, within about 1 month, within about 3 months, or within about 6 months following administration of the pharmaceutical formulation.

For example, the pharmaceutical formulation is administered to the subject in an effective amount to reduce bone loss in the subject as shown by an increase/decrease of an osteoporosis biomarker level in the blood of the subject by at least 5%, at least 10%, at least 15%, at least 20%, at least 25%, or at least 30% compared to the osteoporosis biomarker level in the blood of the subject before treatment; to reduce the body weight, reduce the percentage of fat, and/or reduce the BMI of the subject by at least 5%, at least 10%, at least 15%, at least 20%, at least 25%, or at least 30% compared to the body weight, the percentage of fat, and/or the BMI of the subject before treatment; and to increase the leptin level in the blood of the subject by at least 5%, at least 10%, at least 15%, at least 20%, at least 25%, or at least 30% compared to the leptin level in the blood of subject before treatment, where the increase/decrease of the osteoporosis biomarker level in the blood of the subject, the reduction of the body weight, the percentage of fat, and/or the BMI of the subject, and the increase of the leptin level in the blood of the subject occurs within about 14 days, within about 1 month, within about 3 months, or within about 6 months following administration of the pharmaceutical formulation.

Optionally, the concentration of nanoparticles in the pharmaceutical formulation that is administered to the subject in an effective amount to prevent or reduce bone loss (for example, as shown by an increase/decrease of an osteoporosis biomarker level in the blood), reduce the body weight, reduce the percentage of fat, reduce the BMI, and/or increase the leptin level in the blood of the subject is in a range from about 0.1 μg to about 100 μg, from about 0.5 μg to about 50 μg, from about 1 μg to about 100 μg, from about 1 μg to about 50 μg, from about 1 μg to about 25 μg, from about 1 μg to about 10 μg, from about 1 μg to about 5 μg, from about 4 μg to about 10 μg, from about 1 μg to about 4 μg, from about 2 μg to about 100 μg, from about 2 μg to about 50 μg, from about 2 μg to about 25 μg, from about 2 μg to about 10 μg, from about 2 μg to about 5 μg, from about 2 μg to about 10 μg, or from about 2 μg to about 4 μg per g of the subject.

For example, the concentration of nanoparticles in the pharmaceutical formulation administered to the subject in an effective amount to prevent or reduce bone loss (for example, as shown by an increase/decrease of an osteoporosis biomarker level in the blood), reduce the body weight, reduce the percentage of fat, reduce the BMI, and/or increase the leptin level in the blood of the subject is in a range from about 2 μg to about 10 μg, from about 2 μg to about 4 μg, or from about 4 μg to about 10 μg per g of the subject.

The disclosed nanoparticles, pharmaceutical formulations, and methods of using can be further understood through the following enumerated paragraphs.

1. A plurality of nanoparticles for preventing or reducing peri-/post-menopausal bone loss and/or obesity in a subject, wherein the nanoparticles comprise
   a cage,
   a surface modifying agent,
   a targeting ligand, and
   an active agent,
   wherein the surface modifying agent is attached to an outer surface of the cage and wherein the targeting ligand is exposed to a surrounding environment, and wherein the active agent is encapsulated in the cage.

2. The plurality of nanoparticles of paragraph 1, wherein the cage is a zeolitic imidazolate framework ("ZIF"), and wherein the ZIF comprises a metal ion selected from the group consisting of $Zn^+$, $Zn^{2+}$, $Pd^{2+}$, $Pd^{4+}$, $Pt^{2+}$, $Pt^{4+}$, $Ni^+$, $Ni^{2+}$, $Ni^{3+}$, $Mn^{2+}$, $Mn^{3+}$, $Mn^{4+}$, $Mn^{6+}$, $Mn^{7+}$, $Co^{2+}$, $Co^{3+}$, $Cu^{2+}$, $Cd^{2+}$, $Fe^{2+}$, $Fe^{3+}$, and $Ti^{4+}$.

3. The plurality of nanoparticles of paragraph 2, wherein the ZIF comprises imidazolate functionalized with amine, hydroxyl, thiol, aldehyde, or carboxyl, or a combination thereof.

4. The plurality of nanoparticles of paragraph 2 or 3, wherein the ZIF is ZIF-2, ZIF-3, ZIF-4, ZIF-8, ZIF-10, ZIF-11, ZIF-12, ZIF-14, ZIF-20, ZIF-21, ZIF-60, ZIF-61, ZIF-62, ZIF-64, ZIF-65, ZIF-66, ZIF-67, ZIF-68, ZIF-69, ZIF-70, ZIF-71, ZIF-72, ZIF-73, ZIF-74, ZIF-75, ZIF-76, ZIF-77, ZIF-78, ZIF-81, ZIF-82, ZIF-90, ZIF-91, ZIF-92, ZIF-95, or ZIF-100.

5. The plurality of nanoparticles of any one of paragraphs 1-4, wherein at least 20 wt % (weight of the surface modifying agent conjugated to the targeting ligand/total weight of the surface modifying agent attached to the cage), at least 25 wt %, at least 30 wt %, at least 35 wt %, at least 40 wt %, at least 45 wt %, at least 50 wt %, at least 55 wt %, at least 60 wt %, at least 65 wt %, at least 70 wt %, at least 75 wt %, at least 80 wt %, at least 85 wt %, at least 90 wt %, at least 95 wt %, in a range from 20 wt % to 100 wt %, from 30 wt % to 100 wt %, or from 40 wt % to 100 wt % of the surface modifying agent is conjugated to the targeting ligand.

6. The plurality of nanoparticles of any one of paragraphs 1-5, wherein the end of the surface modifying agent that is attached to the cage comprises a chemical moiety containing one or more negative charges.

7. The plurality of nanoparticles of paragraph 6, wherein the chemical moiety is folate, L-methylfolate, or glutamate, or a combination thereof.

8. The plurality of nanoparticles of any one of paragraphs 1-7, wherein the surface modifying agent comprises a polymer backbone selected from the group consisting of polyalkylene glycol, polylactic acid, polyglycolic acid, poly(lactic-co-glycolic acid), polyanhydrides, poly(ortho)esters, polyurethanes, poly(butyric acid), poly(valeric acid), poly(lactide-coaprolactone), and polyethylenimine, and a copolymer thereof.

9. The plurality of nanoparticles of paragraph 8, wherein the polymer backbone of the surface modifying agent is polyethylene glycol.

10. The plurality of nanoparticles of paragraph 8 or 9, wherein the polymer backbone has a molecular weight in a range from about 1 kDa to about 10 kDa, from about 2 kDa to about 10 kDa, from about 3 kDa to about 10 kDa, from about 4 kDa to about 10 kDa, from about 1 kDa to about 9 kDa, from about 2 kDa to about 9 kDa, from about 3 kDa to about 9 kDa, from about 4 kDa to about 9 kDa, from about 1 kDa to about 8 kDa, from about 2 kDa to about 8 kDa, from about 3 kDa to about 8 kDa, from about 4 kDa to about 8 kDa, from about 1 kDa to about 7 kDa, from about 2 kDa to about 7 kDa, from about 3 kDa to about 7 kDa, from about 4 kDa to about 7 kDa, from about 1 kDa to about 6 kDa, from about 2 kDa to about 6 kDa, from about 3 kDa to about 6 kDa, or from about 4 kDa to about 6 kDa.

11. The plurality of nanoparticles of any one of paragraphs 1-10 having an average diameter in a range from about 10 nm to about 100 nm, from about 10 nm to about 90 nm, from about 10 nm to about 80 nm, from about 20 nm to about 100 nm, from about 20 nm to about 90 nm, from about 20 nm to about 80 nm, from about 30 nm to about 100 nm, from about 30 nm to about 90 nm, or from about 30 nm to about 80 nm.

12. The plurality of nanoparticles of any one of paragraphs 1-11, wherein the surface density of the surface modifying agent ("SMA") on the surface of the nanoparticle is at least 1 SMA/nm$^2$, at least 5 SMA/nm$^2$, at least 7 SMA/nm$^2$, at least 10 SMA/nm$^2$, at least 15 SMA/nm$^2$, at least 20 SMA/nm$^2$, at least 25 SMA/nm$^2$, at least 30 SMA/nm$^2$, at least 35 SMA/nm$^2$, at least 40 SMA/nm$^2$, at least 45 SMA/nm$^2$, or at least 50 SMA/nm$^2$.

13. The plurality of nanoparticles of any one of paragraphs 1-12, wherein the targeting ligand is a gonadotropin-releasing hormone ("GnRH") agonist or a follicle stimulating hormone ("FSH") receptor agonist, or a LH receptor antagonist, or a combination thereof.

14. The plurality of nanoparticles of any one of paragraphs 1-13, wherein the targeting ligand is selected from the group consisting of buserelin, azagly-naflorein, deslorelin, fertirelin, gonadorelin, goserelin, histrelin, lecirelin, leuprorelin, nafarelin, peforelin, peforelin acetate, triptorelin, leuprolide, leuprolide acetate, abarelix, cetrorelix, degarelix, elagolix, ganirelix, linzagolix, relugolix, thiazolidinone compound 5, hexahydroquinoline derivative Org 214444-0, thienopyrimidine derivatives, such as thienopyrimidine derivative Org 43553, 5-amino-N-(tert-butyl)-4-(3-(isonicotinamido)phenyl)-2-(methylthio)thieno-[2,3-d]pyrimidine-6-carboxamide, 5-amino-N-(tert-butyl)-2-(methylthio)-4-(3-(thiophene-3-carboxamido)phenyl thieno[2,3-d]pyrimidine-6-carboxamide, 5-amino-N-(tert-butyl-2-(methylsulfonyl)-4-(3-(nicotinamido)phenyl)thieno[2,3-d]pyrimidine-6-carboxamide, 5-amino-N-(tert-butyl-4-(3-(1-methyl-1H-pyrazole-4-carboxamido)phenyl)-2-(methylsulfanyl)thieno[2,3-d]pyrimidine-6-carboxamide, 5-amino-N-(tert-butyl)-4-(3-(2-metoxynicotinamido)phenyl)-2-(methylthio)thieno[2,3-d]pyrimidine-6-carboxamide, 4-(3-(5-amino-6-(tert-butylcarbamoyl)-2-(methylthio)thieno[2,3-d]pyrimidine-4-il)phenyl)carbamoyl)pyridine 1-oxide, and 5-amino-N-(tert-butyl)-4-(3-(2-chloronicotinamido)phenyl)-2-(methylthio)thieno[2,3-d]pyrimidine-6-carboxamide; diketopiperazines, and m-dihydropyridine, and a combination thereof.

15. The plurality of nanoparticles of any one of paragraphs 1-14, wherein the targeting ligand is buserelin.

16. The plurality of nanoparticles of any one of paragraphs 1-15, wherein the active agent is a ribosome inactivating protein, an apoptosis inducer, a hormone, a receptor ligand, or a nucleic acid, or a combination thereof.

17. The plurality of nanoparticles of any one of paragraphs 1-16, wherein the active agent is saporin, gelonin, a pokeweed antiviral protein, or an apoptosis inducer, or a combination thereof.

18. The plurality of nanoparticles of any one of paragraphs 1-17, wherein one or more of the nanoparticles further comprise a dye encapsulated in the nanoparticle.

19. A pharmaceutical formulation comprising the plurality of nanoparticles of any one of paragraphs 1-18 and a pharmaceutically acceptable carrier and/or excipient.

20. The pharmaceutical formulation of paragraph 19, wherein the pharmaceutical formulation comprises an effective amount of the nanoparticles to reduce or prevent bone loss, reduce body weight, reduce percentage of fat, reduce body mass index (BMI), and/or increase leptin level in the blood of a subject in need thereof.

21. The pharmaceutical formulation of paragraph 20, wherein the effective amount of the nanoparticles is effective to reduce the body weight, reduce the percentage of fat, and/or reduce the body mass index ("BMI") of the subject by at least 5%, at least 10%, at least 15%, at least 20%, at least 25%, or at least 30% compared to the body weight, the percentage of fat, and/or the BMI of the subject before treatment.

22. The pharmaceutical formulation of paragraph 20 or 21, wherein the effective amount of the nanoparticles is effective to reduce bone loss in the subject as shown by an increase or decrease of an osteoporosis biomarker level in the blood of the subject by at least 5%, at least 10%, at least 15%, at least 20%, at least 25%, or at least 30% compared to the osteoporosis biomarker level in the blood of the subject before treatment.

23. The pharmaceutical formulation of paragraph 22, wherein the effective amount of the nanoparticles is effective to reduce bone loss in the subject as shown by an increase of the osteocalcin, bone specific alkaline phosphatase, PINP, and/or PICP level in the blood of the subject by at least 5%, at least 10%, at least 15%, at least 20%, at least 25%, or at least 30% compared to the osteocalcin, bone specific alkaline phosphatase, PINP, and/or PICP level in the blood of the subject before treatment.

24. The pharmaceutical formulation of paragraph 22, wherein the effective amount of the nanoparticles is effective to reduce bone loss in the subject as shown by a decrease of the NTX-1, TRAP5B, osteopontin, and/or bone sialoprotein level in the blood of the subject by at least 5%, at least 10%, at least 15%, at least 20%, at least 25%, or at least 30% compared to the NTX-1, TRAP5B, osteopontin, and/or bone sialoprotein level in the blood of the subject before treatment.

25. The pharmaceutical formulation of any one of paragraphs 20-24, wherein the effective amount of the nanoparticles is effective to increase the leptin level in the blood of the subject by at least 5%, at least 10%, at least 15%, at least 20%, at least 25%, or at least 30% compared to the leptin level in the blood of the subject before treatment.

26. The pharmaceutical formulation of any one of paragraphs 19-25, wherein the concentration of the active agent in the pharmaceutical formulation is in a range from about 0.000001 wt % to 20 wt %, from about 0.000005 wt % to 20 wt %, from about 0.00001 wt % to 20 wt %, from about 0.00005 wt % to 20 wt %, from about 0.0001 wt % to 20 wt %, from about 0.0005 wt % to 20 wt %, from about 0.001 wt % to 20 wt %, from about 0.000001 wt % to 10 wt %, from about 0.000005 wt % to 10 wt %, from about 0.00001 wt % to 10 wt %, from about 0.00005 wt % to 10 wt %, from about 0.0001 wt % to 10 wt %, from about 0.0005 wt % to 10 wt %, from about 0.001 wt % to 10 wt %, from about 0.000001 wt % to 5 wt %, from about 0.000005 wt % to 5 wt %, from about 0.00001 wt % to 5 wt %, from about 0.00005 wt % to 5 wt %, from about 0.0001 wt % to 5 wt %, from about 0.0005 wt % to 5 wt %, from about 0.001 wt % to 5 wt %, from about 0.000001 wt % to 2 wt %, from about 0.000005 wt % to 2 wt %, from about 0.00001 wt % to 2 wt %, from about 0.00005 wt % to 2 wt %, from about 0.0001 wt % to 2 wt %, from about 0.0005 wt % to 2 wt %, from about 0.001 wt % to 2 wt %, from about 0.000001 wt % to 0.5 wt %, from about 0.000005 wt % to 0.5 wt %, from about 0.00001 wt % to 0.5 wt %, from about 0.00005 wt % to 0.5 wt %, from about 0.0001 wt % to 0.5 wt %, from about 0.0005 wt % to 0.5 wt %, from about 0.001 wt % to 0.5 wt %, from about 0.000001 wt % to 0.2 wt %, from about 0.000005 wt % to 0.2 wt %, from about 0.00001 wt % to 0.2 wt %, from about 0.00005 wt % to 0.2 wt %, from about 0.0001 wt % to 0.2 wt %, from about 0.0005 wt % to 0.2 wt %, from about 0.001 wt % to 0.2 wt %, from about 0.000001 wt % to 0.05 wt %, from about 0.000005 wt % to 0.05 wt %, from about 0.00001 wt % to 0.05 wt %, from about 0.00005 wt % to 0.05 wt %, from about 0.0001 wt % to 0.05 wt %, from about 0.0005 wt % to 0.05 wt %, from about 0.001 wt % to 0.05 wt %, from about 0.000001 wt % to 0.02 wt %, from about 0.000005 wt % to 0.02 wt %, from about 0.00001 wt % to 0.02 wt %, from about 0.00005 wt % to 0.02 wt %, from about 0.0001 wt % to 0.02 wt %, from about 0.0005 wt % to 0.02 wt %, from about 0.001 wt % to 0.02 wt %, from about 0.000001 wt % to 0.005 wt %, from about 0.000005 wt % to 0.005 wt %, from about 0.00001 wt % to 0.005 wt %, from about 0.00005 wt % to 0.005 wt %, from about 0.0001 wt % to 0.005 wt %, from about 0.0005 wt % to 0.005 wt %, from about 0.000001 wt % to 0.002 wt %, from about 0.000005 wt % to 0.002 wt %, from about 0.00001 wt % to 0.002 wt %, from about 0.00005 wt % to 0.002 wt %, from about 0.0001 wt % to 0.002 wt %, or from about 0.0005 wt % to 0.002 wt %.

27. The pharmaceutical formulation of any one of paragraphs 19-26, in a unit dosage form, wherein the dosage of the active agent is in a range from about $5\times10^{-5}$ µg to about 0.5 µg, from about $5\times10^{-5}$ µg to about 0.1 µg, from about $5\times10^{-5}$ µg to about 0.01 µg, from about $5\times10^{-5}$ µg to about 0.005 µg, from about $5\times10^{-5}$ µg to about 0.001 µg, from about $5\times10^{-5}$ µg to about $5\times10^{-4}$ µg, from about $1\times10^{-4}$ µg to about 0.5 µg, from about $5\times10^{-4}$ µg to about 0.5 µg, from about 0.001 µg to about 0.5 µg, or from about 0.01 µg to about 0.5 µg.

28. The pharmaceutical formulation of any one of paragraphs 19-27 in a form suitable for intramuscular administration, intravenous administration, intraperitoneal administration, or subcutaneous administration, or a combination thereof.

29. A method for preventing or reducing peri-/post-menopausal bone loss and/or obesity in a subject in need thereof comprising (i) administering to the subject the pharmaceutical formulation of any one of paragraphs 19 to 28, wherein step (i) occurs one or more times.

30. The method of paragraph 29, comprising only a single administration of the pharmaceutical formulation, wherein the pharmaceutical formulation comprises an effective amount of the nanoparticles to prevent or reduce bone loss as shown by an increase or decrease of an osteoporosis biomarker level in the blood, increase the leptin level in the blood, reduce body weight, reduce percentage of fat, and/or reduce body mass index (BMI) of the subject.

31. The method of paragraph 29, comprising more than one step of administering to the subject the pharmaceutical formulation, wherein following all of the administration steps an effective amount of the nanoparticles to reduce or prevent bone loss as shown by an increase or decrease of an osteoporosis biomarker level in the blood, increase the leptin level in the blood, reduce body weight, reduce percentage of fat, and/or reduce body mass index (BMI) of the subject is administered to the subject.

32. The method of any one of paragraphs 29 to 31, wherein the subject is a peri/post-menopausal mammal.

33. The method of any one of paragraphs 29 to 32, wherein in step (i) the pharmaceutical formulation is administered by intramuscular administration, intravenous administration, intraperitoneal administration, or subcutaneous administration, or a combination thereof.

34. The method of any one of paragraphs 26 to 30, wherein during step (i), the dosage of the nanoparticles in the pharmaceutical formulation is from about 0.1 µg to about 100 µg, from about 0.5 µg to about 50 µg, from about 1 µg to about 100 µg, from about 2 µg to about 100 µg, from about 2 µg to about 50 µg, from about 2 µg to about 25 µg, from about 2 µg to about 10 µg, from about 2 µg to about 5 µg, from about 4 µg to about 10 µg, or from about 2 µg to about 4 µg per g of the subject.

35. The method of any one of paragraphs 30 to 34, wherein the reduction of the body weight, the percentage of fat, and/or the BMI of the subject occurs within about 14 days, within about 1 month, within about 3 months, or within about 6 months following step (i).

36. The method of any one of paragraphs 30 to 35, wherein the increase of the leptin level in the blood of the subject occurs within about 14 days, within about 1 month, within about 3 months, or within about 6 months following step (i).

37. The method of any one of paragraphs 30 to 36, wherein the increase or decrease of the osteoporosis biomarker level in the blood of the subject occurs within about 14 days, within about 1 month, within about 3 months, or within about 6 months following step (i).

The present invention will be further understood by reference to the following non-limiting examples.

EXAMPLES

Example 1. Structure and Properties of Exemplary Organic Nanoparticles

Material and Methods
Preparation of GnRH Nanoparticles

There are four major steps in the preparation of GnRH nanoparticles [BUS-PEG-(CF647-SAP@ZIF)]. They are as follows: (1) conjugation of CF647-SAP; (2) conjugation of BUS-PEG-FA; (3) synthesis of CF647-SAP@ZIF; (4) prepare BUS-PEG-(CF647-SAP@ZIF).

(1) Conjugation of the Dye CF647 with Saporin (SAP)

The conjugation of CF647-SAP was accomplished by dissolving 1 mg SAP in 1 mL of 0.1 M sodium bicarbonate buffer (pH 8.3) and 52.4 µl 10 mM CF647 succinimidyl ester dyes in DMSO to react for 1 hour at room temperature. The purified conjugation of CF647-SAP was obtained by using ultrafiltration devices (Amicon Ultra-2 Centrifugal Filter Unit) and the concentration was characterized by UV-Vis absorbance spectrometer (Shimadzu UV-2450).

(2) Conjugation of Buserelin (BUS) to PEG-FA

The conjugation of BUS-PEG-FA was obtained by reacting 10 mg BUS and 50 mg FA-PEG-NHS in PBS buffer (pH=7.4) for 1 h. The conjugation of BUS-PEG-FA was purified by ultrafiltration devices (Amico Ultra-15 Centrifugal Filter Unit), and then freeze-dried under vacuum.

(3) Synthesis of CF647-SAP@ZIF

CF647-SAP@ZIF nanoparticles were synthesized via rapid pouring 0.5875 g Zinc nitrate hexahydrates (in 4 g water) into an aqueous solution containing 11.35 g 2-methylimidazole, 722 µg CF647-SAP and 40 g water to form CF647-SAP@ZIF nanoparticles 30 min after the reaction at room temperature. The product was washed and collected by centrifugation.

(4) Preparation of BUS-PEG-(CF647-SAP@ZIF)

100 mg of the as-synthesized CF646-SAP@ZIF nanoparticles was dispersed in 10 mg/mL BUS-PEG-FA water solution, and then stirred for 48 h under room temperature. Then the BUS-PEG-(CF647-SAP@ZIF) product was collected by centrifugation, and then freeze-dried under vacuum for long-term storage.

The resulting BUS-PEG-modified ZIF nanoparticles containing the dye CF647 and active agent, saporin, encapsulated therein are referred to in the Examples as "GnRH nanoparticles" or "GnRH NPs".

Morphology and Fluorescence of GnRH Nanoparticles

The size of the nanoparticles was determined using scanning electron microscopy. The morphology of the ZIF NPs was assessed using a field emission gun scanning electron microscope (FEG-SEM, FEI Inspect F). Fluorescent properties of ZIF, ZIF with CF647 and saporin encapsulated therein, and BUS-PEG-modified ZIF with CF647 and SAP encapsulated therein ("GnRH NP") were analyzed using a Horiba FluoroLog-3 spectrofluorometer (Horiba Scientific, Edison, NJ, USA) equipped with a 450-W xenon arc lamp, a photomultiplier tube (measurement range, 240-850 nm).

Purity of GnRH NPs

Core bulk samples prepared for X-ray diffraction (XRD) were air-dried and powdered for random particle orientation and mounting as a pressed powder. Sample was ground briefly with mortar and pestle. XRD patterns were collected using a Bruker D8 Advance diffractometer. Instrument conditions included using $CoK\alpha$ radiation (generated at 35 kV and 40 mA), 217.5 mm goniometer radius, 0.6 mm primary slit, Fe-filter, and a Lynx-Eye position sensitive solid-state detector. XRD scan parameters were run at 0.3 s/step in 0.01° 2θ step increments. Data was processed using Bruker Eva software, which includes background correction, $K\alpha 2$ stripping and peak d-spacing and intensity assignments. The peak file generated from the peak search was compared to the International Center for Diffraction Data (ICDD) Powder Diffraction File (PDF-4+ 2018).

Results

Figure 1B:
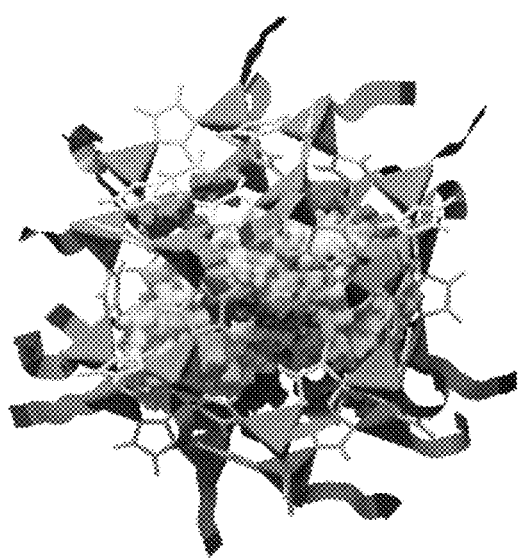
FIG. 1B is a schematic of the structure of an exemplary nanoparticle that contains a zeolitic imidazolate framework ("ZIF") cage, folic acid ("FA") conjugated PEG, FA and Buserelin ("BUS") conjugated PEG, saporin ("SAP"), and CF647.
Figure 1C:
FIG. 1C is a schematic of the structure of an exemplary nanoparticle that contains a ZIF cage, FA and Buserelin ("BUS") conjugated PEG, and saporin ("SAP").

FIG. 1A shows the components of the exemplary organic nanoparticle before assembling. As shown in FIG. 1A, each organic nanoparticle contains a ZIF cage made from $Zn^{2+}$ and imidazole, folic acid ("FA") conjugated PEG, FA and buserelin ("BUS") conjugated PEG, an active agent (i.e. saporin), and optionally dye molecules (i.e. CF647). FIG. 1B shows the structure of an assembled GnRH nanoparticle. FIG. 1C shows the structure of an assembled GnRH nanoparticles that does not include a dye molecule. As shown in FIG. 1B, the surface of the ZIF cage is tagged with Buserelin, a drug that acts as a GnRH agonist. Buserelin binds to receptors that are present on gonadotrophs in the pituitary. Saporin, which is a ribosome inactivating protein, and CF647 are encapsulated in the core of the organic nanoparticle. FIGS. 1A and 1B are schematics of the different components in each organic nanoparticle (the components are not shown to scale).

Figure 2:
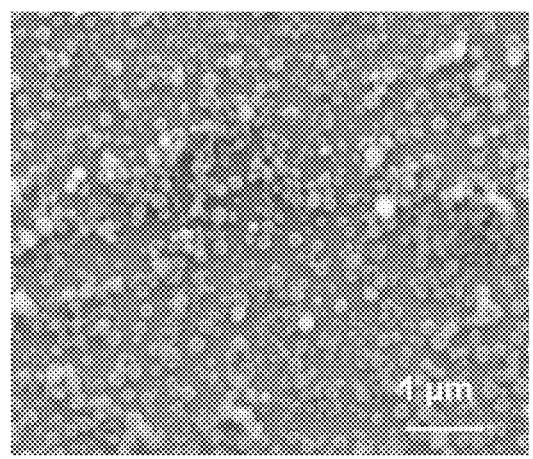
FIG. 2 shows a scanning electron microscope ("SEM") image of exemplary GnRH NPs.
Figure 3A:
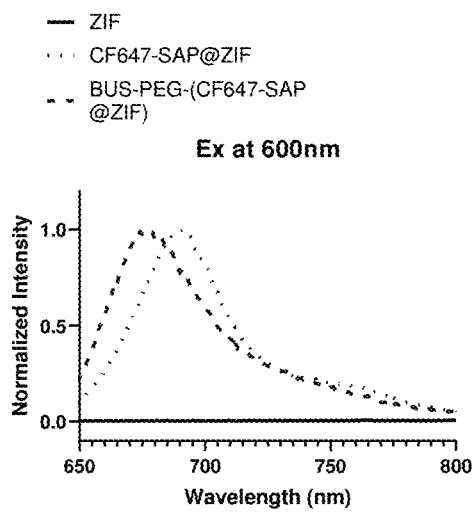
FIGS. 3A-3B are graphs showing the fluorescent property of three types of nanoparticles: ZIF, ZIF with CF647 and SAP encapsulated therein, and GnRH NPs, analyzed using a Horiba FluoroLog-3 spectrofluorometer (Horiba Scientific, Edison, NJ, USA) equipped with a 450-W xenon arc lamp, a photomultiplier tube (measurement range, 240-850 nm).
Figure 3B:
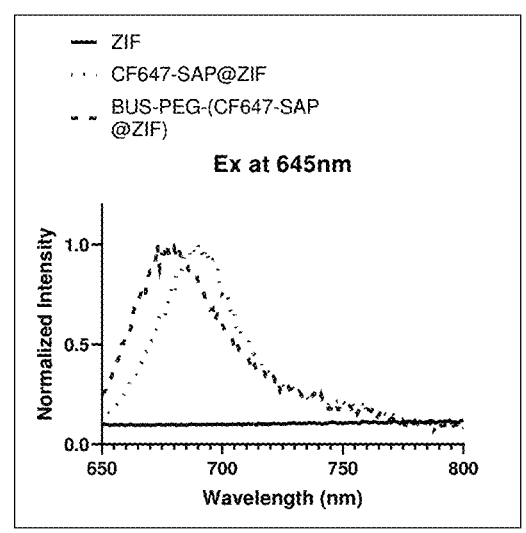
Figure 4:
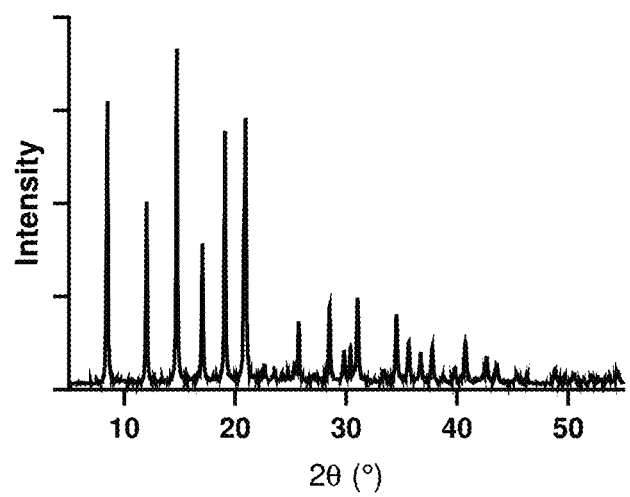
FIG. 4 is a graph showing X-ray diffraction analysis of GnRH nanoparticles (NPs). The peak file generated from the peak search was compared to the International Center for Diffractation Data (ICDD) powder diffraction file. The patterns match with PDF #00-066-0916 as ZIF-90 (91% match).

As shown in FIG. 2, the sizes of GnRH nanoparticles are between 60 nm and 130 nm (including PEG). As shown in FIGS. 3A and 3B, the GnRH nanoparticles emit light (shown in dashed lines) with a maximum intensity at about 665 nm, when excited at two different wavelengths, i.e. 600 nm (FIG. 3A) and 645 nm (FIG. 3B), demonstrating the formation of the nanoparticles. Additionally, as shown in FIG. 4, XRD analysis of the GnRH nanoparticles shows that the patterns are 91% matches to PDF #00-066-0916 as ZIF-90 crystal structure.

Example 2. The Organic Nanoparticles Inhibit Pituitary Cell Viability

Materials and Methods

Solutions of GnRH nanoparticles in PBS were tested in RC4B/C pituitary cells. Pituitary cells were plated into a 96-well plate at the density of $3\times10^5$ cells/cm$^2$ and cultured in vitro in complete medium under standard conditions (i.e. 37° C., 5% $CO_2$, 95% humidity) for 3 days. They were exposed to varying concentrations of the GnRH nanoparticles or an unconjugated ZIF nanoparticle for 1 hour, and then medium was refreshed (to remove the nanoparticles) and the cells were in culture for the following 3 days before being used in the MTT assay. The unconjugated ZIF nanoparticle contains all the elements of the GnRH nanoparticles expect for BUS. The concentrations of each nanoparticle-containing solution were 2, 5, 10, 25, 50, 75, and 100 µg/mL. At the end of this period, the cells were subjected to an MTT assay (Cat No. 30-1010K, ATCC) to measure cell viability.

Results

Figure 5:
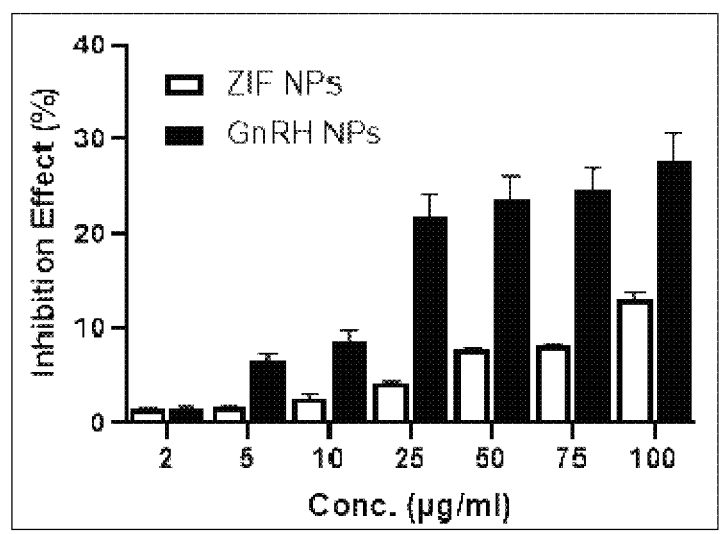
FIG. 5 is a bar graph showing the inhibition effect (%) of RC4B/C pituitary cells by unconjugated ZIF NPs or GnRH NPs at varied concentrations.

Solutions containing 25 µg/ml or more of the GnRH nanoparticles, resulted in 23-28% inhibition of growth of RC4B/C pituitary cells, demonstrating that the GnRH nanoparticles affect about 25% of the cell population that accounts for FSH and LH producing cells (FIG. 5).

Example 3. The Organic Nanoparticles Bind to Gonadotrophs in the Pituitary in Rats Material and Methods Short-Term and Long-Term Nanoparticle Tissue Accumulation Adult female Holtzman Sprague Dawley rats were injected intravenously with phosphate buffered saline (PBS)-control or with a solution of GnRH nanoparticles in PBS (1 µg/g body weight). The rats were sacrificed 3 hours or 3 weeks later; and their organs were harvested and subjected to imaging using IVIS.

Nanoparticles in the Pituitary

Female Holtzman Sprague Dawley rats were injected intravenously with a solution of GnRH nanoparticles in PBS at a rate of 1 µg/g body weight (low dose) or phosphate buffered saline ("PBS", control). Three hours later, they were sacrificed. The pituitary was removed, fixed in formalin, and made into paraffin blocks. Sections were examined under a confocal microscope to determine localization of the nanoparticles.

To confirm the binding of the nanoparticles to the gonadotrophs in pituitary, pituitaries from animals that were injected with the GnRH nanoparticle solutions or PBS as described above were sacrificed 3 hours after administration. Sections of pituitary were treated with antibody for LH to show the location of gonadotrophs. They were examined under a confocal microscope.

Results

Images of the organs of rats from the control group and treated GnRH NP-treated group were reviewed. IVIS imaging of tissues from animals injected with GnRH nanoparticles and sacrificed 3 hours following injection showed the presence of the nanoparticles in the brain and pituitary, which are rich in GnRH receptors (data not shown). The GnRH nanoparticles were also seen in liver and kidney, where the nanoparticles are metabolized and cleared, respectively (data not shown). No nanoparticles associated fluorescence was observed in the heart and the spleen. In contrast, no fluorescence was detected in in any tissue in the PBS-treated animals. When animals were sacrificed 3 weeks following injection of GnRH NP, the nanoparticles were not seen in any of the organs, demonstrating that the particles were completely cleared out of the system (data not shown).

Confocal images of sections of the pituitary from animals injected intravenously with the GnRH nanoparticle solutions or PBS show that the nanoparticles were localized to specific cell populations in the pituitary of the rat 3 hours after injection and were absent 3 weeks after injection (data not shown). To confirm that the GnRH nanoparticles specifically binds to the gonadotrophs in pituitary, sections of pituitary were treated with antibody for LH to localize gonadotrophs. The confocal images of LH-stained gonadotrophs of the pituitary showed green fluorescence (data not shown). The confocal images of the GnRH nanoparticles showed red fluorescence (data not shown). The yellow fluorescence observed in the merged images of labeled gonadotrophs and GnRH nanoparticles demonstrated that location of the nanoparticles was in the LH-stained gonadotrophs (data not shown).

We claim:

1. A pharmaceutical formulation for preventing or reducing peri-/post-menopausal bone loss and/or obesity in a subject comprising
   (a) a plurality of nanoparticles, wherein the nanoparticles comprise
   a cage,
   a surface modifying agent,
   a targeting ligand, and
   an active agent,
   wherein the cage is a zeolitic imidazolate framework ("ZIF")
   wherein the surface modifying agent is attached to an outer surface of the cage and wherein the targeting ligand is exposed to a surrounding environment,
   wherein the targeting ligand is a gonadotropin-releasing hormone ("GnRH") receptor agonist, or a follicle stimulating hormone ("FSH") receptor agonist, or a luteinizing hormone ("LH") receptor agonist, or a combination thereof, and
   wherein the active agent is encapsulated in the cage; and
   (b) a pharmaceutically acceptable carrier and/or excipient.

2. The pharmaceutical formulation of claim 1, wherein the pharmaceutical formulation comprises an effective amount of the nanoparticles to reduce or prevent bone loss, reduce body weight, reduce percentage of fat, reduce body mass index (BMI), and/or decrease leptin level in the blood of a subject in need thereof.

3. The pharmaceutical formulation of claim 2, wherein the effective amount of the nanoparticles is effective to reduce the body weight, reduce the percentage of fat, and/or reduce the body mass index ("BMI") of the subject by at least 5%, at least 10%, at least 15%, at least 20%, at least 25%, or at least 30% compared to the body weight, the percentage of fat, and/or the BMI of the subject before treatment.

4. The pharmaceutical formulation of claim 2, wherein the effective amount of the nanoparticles is effective to reduce bone loss in the subject as shown by an increase or decrease of an osteoporosis biomarker level in the blood of the subject by at least 5%, at least 10%, at least 15%, at least 20%, at least 25%, or at least 30% compared to the osteoporosis biomarker level in the blood of the subject before treatment.

5. The pharmaceutical formulation of claim 2, wherein the effective amount of the nanoparticles is effective to decrease the leptin level in the blood of the subject by at least 5%, at least 10%, at least 15%, at least 20%, at least 25%, or at least 30% compared to the leptin level in the blood of the subject before treatment.

6. The pharmaceutical formulation of claim 1, wherein the pharmaceutical formulation is in a form suitable for intramuscular administration, intravenous administration, intraperitoneal administration, or subcutaneous administration, or a combination thereof.

7. A method for reducing peri-/post-menopausal bone loss and/or obesity in a subject in need thereof comprising
   (i) administering to the subject the pharmaceutical formulation of claim 1, wherein step (i) occurs one or more times.

8. The pharmaceutical formulation of claim 1, wherein the ZIF comprises a metal ion selected from the group consisting of $Zn^+$, $Zn^{2+}$, $Pd^{2+}$, $Pd^{4+}$, $Pt^{2+}$, $Pt^{4+}$, $Ni^+$, $Ni^{2+}$, $Ni^{3+}$, $Mn^{2+}$, $Mn^{3+}$, $Mn^{4+}$, $Mn^{6+}$, $Mn^{7+}$, $Co^{2+}$, $Co^{3+}$, $Cu^{2+}$, $Cd^{2+}$, $Fe^{2+}$, $Fe^{3+}$, and $Ti^{4+}$.

9. The pharmaceutical formulation of claim 1, wherein the ZIF comprises imidazolate functionalized with amine, hydroxyl, thiol, aldehyde, or carboxyl, or a combination thereof.

10. The pharmaceutical formulation of claim 1, wherein the ZIF is ZIF-2, ZIF-3, ZIF-4, ZIF-8, ZIF-10, ZIF-11, ZIF-12, ZIF-14, ZIF-20, ZIF-21, ZIF-60, ZIF-61, ZIF-62, ZIF-64, ZIF-65, ZIF-66, ZIF-67, ZIF-68, ZIF-69, ZIF-70, ZIF-71, ZIF-72, ZIF-73, ZIF-74, ZIF-75, ZIF-76, ZIF-77, ZIF-78, ZIF-81, ZIF-82, ZIF-90, ZIF-91, ZIF-92, ZIF-95, or ZIF-100.

11. The pharmaceutical formulation of claim 1, wherein at least 20 wt %, at least 25 wt %, at least 30 wt %, at least 35 wt %, at least 40 wt %, at least 45 wt %, at least 50 wt %, at least 55 wt %, at least 60 wt %, at least 65 wt %, at least 70 wt %, at least 75 wt %, at least 80 wt %, at least 85 wt %, at least 90 wt %, at least 95 wt %, in a range from 20 wt % to 100 wt %, from 30 wt % to 100 wt %, or from 40 wt % to 100 wt % of the surface modifying agent is conjugated to the targeting ligand.

12. The pharmaceutical formulation of claim 1, wherein the end of the surface modifying agent that is attached to the cage comprises a chemical moiety containing one or more negative charges.

13. The pharmaceutical formulation of claim 12, wherein the chemical moiety is folate, L-methylfolate, or glutamate, or a combination thereof.

14. The pharmaceutical formulation of claim 1, wherein the surface modifying agent comprises a polymer backbone selected from the group consisting of polyalkylene glycol, polylactic acid, polyglycolic acid, poly(lactic-co-glycolic acid), polyanhydrides, poly(ortho) esters, polyurethanes, poly(butyric acid), poly(valeric acid), poly(lactide-coaprolactone), and polyethylenimine, and a copolymer thereof.

15. The pharmaceutical formulation of claim 14, wherein the polymer backbone has a molecular weight in a range from about 1 kDa to about 10 kDa, from about 2 kDa to about 10 kDa, from about 3 kDa to about 10 kDa, from about 4 kDa to about 10 kDa, from about 1 kDa to about 9 kDa, from about 2 kDa to about 9 kDa, from about 3 kDa to about 9 kDa, from about 4 kDa to about 9 kDa, from about 1 kDa to about 8 kDa, from about 2 kDa to about 8 kDa, from about 3 kDa to about 8 kDa, from about 4 kDa to about 8 kDa, from about 1 kDa to about 7 kDa, from about 2 kDa to about 7 kDa, from about 3 kDa to about 7 kDa, from about 4 kDa to about 7 kDa, from about 1 kDa to about 6 kDa, from about 2 kDa to about 6 kDa, from about 3 kDa to about 6 kDa, or from about 4 kDa to about 6 kDa.

16. The pharmaceutical formulation of claim 1, having an average diameter in a range from about 10 nm to about 100 nm, from about 10 nm to about 90 nm, from about 10 nm to about 80 nm, from about 20 nm to about 100 nm, from about 20 nm to about 90 nm, from about 20 nm to about 80 nm, from about 30 nm to about 100 nm, from about 30 nm to about 90 nm, or from about 30 nm to about 80 nm.

17. The pharmaceutical formulation of claim 1, wherein the surface density of the surface modifying agent ("SMA") on the surface of the nanoparticle is at least 1 SMA/nm$^2$, at least 5 SMA/nm$^2$, at least 7 SMA/nm$^2$, at least 10 SMA/nm$^2$, at least 15 SMA/nm$^2$, at least 20 SMA/nm$^2$, at least 25 SMA/nm$^2$, at least 30 SMA/nm$^2$, at least 35 SMA/nm$^2$, at least 40 SMA/nm$^2$, at least 45 SMA/nm$^2$, or at least 50 SMA/nm$^2$.

18. The pharmaceutical formulation of claim 1, wherein the active agent is a ribosome inactivating protein, an apoptosis inducer, a hormone, a receptor ligand, or a nucleic acid, or a combination thereof.

19. The pharmaceutical formulation of claim 14, wherein the polymer backbone of the surface modifying agent is polyethylene glycol.

* * * * *